(12) United States Patent
DuFour

(10) Patent No.: US 7,238,339 B2
(45) Date of Patent: Jul. 3, 2007

(54) BIFUNCTIONAL CHELATING COMPOUNDS CONTAINING HYDROXAMIC ACID RESIDUES

(75) Inventor: Jean-Marc DuFour, Pierrefonds (CA)

(73) Assignee: DRAXIS Specialty Pharmaceuticals Inc., Kirkland, Quebec (CA)

(*) Notice: Subject to any disclaimer, the term of this patent is extended or adjusted under 35 U.S.C. 154(b) by 0 days.

(21) Appl. No.: 10/634,335

(22) Filed: Aug. 4, 2003

(65) Prior Publication Data

US 2004/0086460 A1 May 6, 2004

Related U.S. Application Data

(62) Division of application No. 09/739,436, filed on Dec. 18, 2000, now Pat. No. 6,623,721.

(51) Int. Cl.
*A61K 51/00* (2006.01)
*A61M 36/14* (2006.01)
(52) U.S. Cl. .................. 424/1.65; 424/1.11; 424/1.81; 534/14; 534/15; 534/16; 562/620
(58) Field of Classification Search .................. 534/7, 534/10–16; 424/1.11, 1.65, 1.69, 1.73, 9.1, 424/9.2, 9.3, 9.4, 9.5, 9.6, 9.7, 9.8; 562/1, 562/400, 620
See application file for complete search history.

(56) References Cited

U.S. PATENT DOCUMENTS

| 4,256,765 | A | 3/1981 | Munakata et al. ........... 424/315 |
| 4,741,887 | A | 5/1988 | Coleman et al. ............. 423/112 |
| 5,539,138 | A | 7/1996 | Flanagan et al. .............. 558/17 |
| 5,556,939 | A | 9/1996 | Flanagan et al. ............ 530/311 |
| 5,632,969 | A | 5/1997 | Flanagan et al. ........... 424/1.69 |
| 5,733,342 | A | 3/1998 | Greindl et al. .................. 8/137 |
| 5,756,825 | A | 5/1998 | Safavy et al. ................ 560/169 |

FOREIGN PATENT DOCUMENTS

| WO | 92/20227 | 11/1992 |
| WO | 93/00082 | 1/1993 |
| WO | 94/05627 | 3/1994 |

OTHER PUBLICATIONS

Altenburger, J.M., et al., "Useful hydroxylamine derivatives for the synthesis of hydroxamic acids," Received in France Mar. 20, 1992, 5055-5058.
Atherton, E., et al., "Peptide synthesis. Part 10. Use of pentafluorophenyl esters of fluorenyl methoxycarbonylamino acids in solid phase peptide synthesis," *Tetra. Letts.*, 1998, 44(3), 843-857.
Bergeron, R.J., et. al., "Synthesis and biological evaluation of hydroxamate-based iron chelators," *J. Medicinal Chem.*, 1991, 34, 3182-3187.
Bergeron, R.J., et al., "The total synthesis of desferrioxamines E and G," *Tetrahedron*, 1990, 46(17), 5581-5888.

Bergeron, R.J., et al., "The total synthesis of alcaligin," *J. Org. Chem.*, 1991, 56, 5560-5563.
Bergeron, R.J., et al., "The total synthesis of bisucaberin," *Tetrahedron*, 1989, 45(16), 4939-4944.
Carpino, L.A., et al., "O-Acylhydroxylamines. I. Synthesis of O-Benzoylhydroxylamine," *J. Am. Chem. Soc.*, 81, 1959, 955-957.
Castro, J.L., et al., "Mitsunobu-like processes with a novel triphenylphosphine-cyclic sulfamide betaine," *J. Org. Chem.*, 1994, 59(9), 2289-2291.
Chaubet, F., et al., "The design of magnetic resonance contrast agents: new iron (III) dihydroxamate complexes," *Tetra. Letts.*, 1990, 31(40), 5729-5732.
Chaudhary, S.K., et al., "4-dimethylaminopyridine: an efficient and selective catalyst for the silyation of alcohols," *Pergamon Press Ltd.*, 1979, 20(2), 99-102.
Gibson, F.S., et al., "Selective removal of an N-BOC protecting group in the presence of a tert-butyl ester and other acid-sensitive groups," *J. Org. Chem.*, 1994, 59(11), 3216-3218.
Henry, J.R., et al., "Mitsunobu reactions of N-Alkyl and N-Acyl sulfonamides-an efficient route to protected amines," *Tetra. Letts.*, 1989, 30(42), 5709-5712.
Hou, Z., et al., "Preorganization of ferric alcaligin, $Fe_2L_3$. The first structure of a ferric dihydroxamate siderophore," *Am. Chem. Soc.*, 1996, 118(21), 5148-5149.
Huffman, W.F., et al., "Nuclear analogues of β-lactam antibiotics. 2. the total synthesis of 8-Oxo-4-thia-1-azabicyclo[4.2.0]oct-2-ene-2-carboxylic acids," *J. Am. Chem. Soc.*, 1977, 99.7, 3 pages.
Iida, H., et al., "An efficient, fully stereocontrolled total synthesis of N-Benzoyl-$_L$-daunosamine," *J. Org. Chem.*, 1986, 51(22), 4245-4249.
Karunaratne, V., et al., "General method for the synthesis of trishydroxamic acids," *Tetra. Letts.*, 1992, 33(14), 1827-1830.
Katoh, A., et al., "N-hydroxy amides. Part 9. Synthesis and iron (III) complexes of tripodal hydroxamic acids derived from ω-(N-Hydroxyamino)alkanoic acids and tris-(2-aminoethyl)amine," *J. Chem. Soc. Perkin Trans.*, 1991, 1839-1842.
Koshti, N.M. et al., "Convenient method for the preparation of some polyhydroxamic acids: Michael addition of amines to acrylohydroxamic acid derivatives," *Tetra. Letts.*, 1994, 35(29), 5157-5160.
Lee, B.H., et al., "Natural ferric ionophores: Total synthesis of schizokinen, schizokinen A, and arthrobactin," *J. Org. Chem.*, 1983, 48(1), 24-31.
Miller, M.J., "Hydroxamate approach to the synthesis of β-lactam antibiotics," *Acc. Chem Res.*, 1986, 19, 49-56.
Nikam, S.S., et al., "Synthesis of hydroxamic acids: $Pd/BaSO_4$ as a new catalyst for the deprotection of o-benzyl hydroxamates," *Tetra. Letts.*, 1995, 36(2), 197-200.

(Continued)

*Primary Examiner*—D.L. Jones
(74) *Attorney, Agent, or Firm*—Woodcock Washburn LLP

(57) ABSTRACT

New types of hydroxamic acid-based bifunctional chelators are provided. These chelators are designed to chelate metal ions that can be detected either by their paramagnetic or radioactive properties. Conjugation with peptides or protein can be achieved by the presence of a linker moiety in the molecular structure of these chelators.

23 Claims, 6 Drawing Sheets

OTHER PUBLICATIONS

Rajappa, S., et al., "Hydroxamic acids and their derivatives-III; Preparation of esters of pivalohydroxamic acid and their use in peptide synthesis," *Tetrahedron*, 1967, 23, 4805-4809.

Ramalingam, K., et al., "Synthesis of nitroimidazole substituted 3,3,9,9-tetramethyl-4,8-diazaundecane-2,10-dione dioximes (propylene amine oximes, PnAOs): ligands for technetium-99m complexes with potential for imaging hypoxic tissue," *Tetrahedron*, 1995, 51(10), 2875-2894.

Safavy, A., et al., "Synthesis of N-[tris[2-[[N-(benzyloxy)amino]carbonyl]ethyl]succinamic acid, trisuccin. Hydroxamic acid derivatives as a new class of bifunctional chelating agents," *Bioconjugate Chem.*, 1993, 4(3), 194-198.

Sandler, S.R., et al., "Chapter 12/Hydroxamic Acids," *Org. Functional Group Preparations*, 1972, 3, 406-447.

Spanevello, R.A., et al., "synthesis of novel, highly potent cyclic-hexapeptide analogs of somatostatin. Potential application of orthogonal protection for affinity chromatography," *Tetra. Letts.*, 1991, 32(36), 4675-4678.

Still, W.C., et al., "Rapid chromatographic technique for preparative separations with moderate resolution," *J. Am. Chem. Soc.*, 1978, 43(14), 2923-2925.

Sun, Y., et al., "Synthesis and characterization of a new macrobicyclic (cryptand) siderophore containing three endocyclic hydroxamate donor groups," *Tetrahedron*, 1990, 46(8), 2725-2736.

Wadsworth, D.H., "Azetidine," *Org. Syntheses Coll.*, 1988, vol. VI, 75-77.

BIFUNCTIONAL CHELATING COMPOUNDS CONTAINING HYDROXAMIC ACID RESIDUES

CROSS REFERENCE TO RELATED APPLICATIONS

This application is a division of U.S. patent application Ser. No. 09/739,436, filed Dec. 18, 2000 now U.S. Pat. No. 6,623,721, the contents of which are hereby incorporated herein by reference in its entirety.

FIELD OF THE INVENTION

This application is directed to new types of hydroxamic acid-based bifunctional chelators. These chelators preferably chelate metal ions that can be detected either by their paramagnetic or radioactive properties.

BACKGROUND OF THE INVENTION

Natural substances containing hydroxamic acid functionalities in their structures exhibit a wide variety of biological activities. Frequently, they act in vivo as antibiotics, growth factors, and iron-transport agents. Siderophores represent one type of natural substance that contain hydroxamic acid functionalities. Siderophores are small iron-chelating molecules produced by the organism when iron deficiencies occur. There are mainly two classes of siderophores, the cathecolamides and the hydroxamates. The cathecolamide class includes, for example, parabactin and vibriobactin. The hydroxamate class includes, for example, bisucaberin (macrocyclic), desferrioxamine B (linear), desferrioxamine G (linear) and desferrioxamine E (macrocyclic). Because of their numerous potential applications, such as in the treatment of iron overload, also known as Cooley's anemia, as contrast agents for NMR imaging, and as diagnostic and therapeutic radiopharmaceuticals, the design and synthesis of new chelators possessing hydroxamic acid residues have attracted the attention of several research groups.

OBJECTS OF THE INVENTION

It is one object of this invention to provide chelators that can be attached to peptides and proteins by forming a thiourea or amide bond.

It is a further object of this invention to provide compounds that include diagnostic and therapeutic agents.

It is yet another object of this invention to provide improvements in research and diagnostic methods and materials for assaying bodily states in animals, especially disease states.

BRIEF DESCRIPTION OF THE INVENTION

These and other objects are satisfied by the present inventions, which in one aspect provide chelators that can be attached to peptides or proteins. The chelators of the invention generally possess hydroxamic acid functionalities and can be bound to peptides and/or proteins, by forming a thiourea or amide bond. Preferred chelators have any of the formulas I, II, or III:

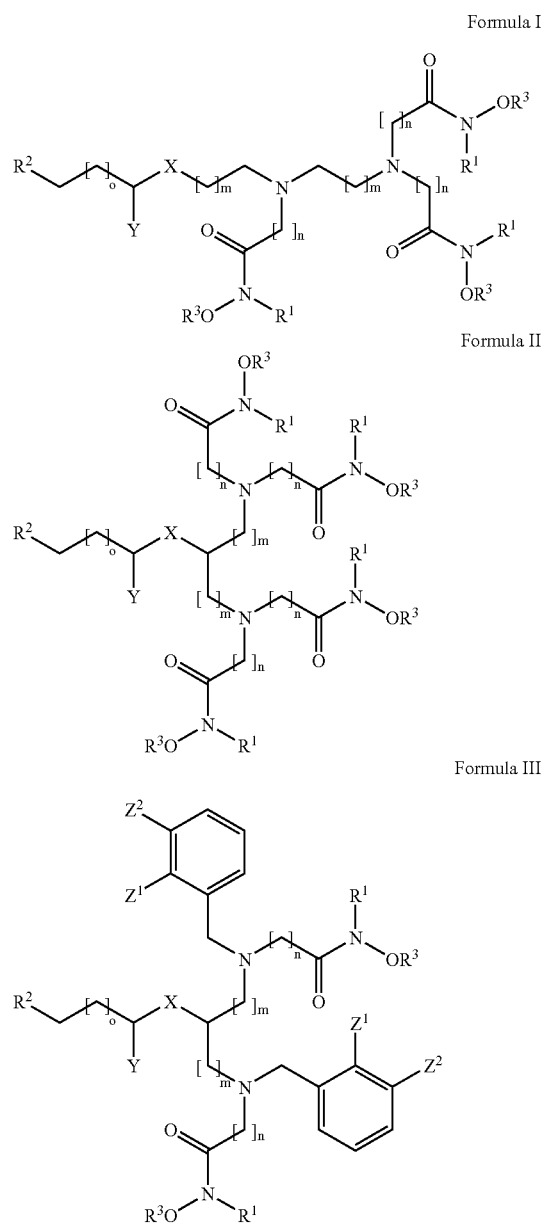

where n, m and o are, independently, an integer from 1 to about 4;

X is $CH_2$, nitrogen ($N(R^4)$), oxygen or sulfur;

Y is hydrogen, —OH (hydroxyl), =O (carbonyl), $N(R^4)(R^5)$, or =S;

$R^1$ is hydrogen, alkyl having 1 to 5 carbon atoms, or a protective group;

$R^2$ is an active group such as an activated ester, a carboxylic acid, an alkyl isothiocyanate, an aromatic isothiocyanate or a leaving group (such as I, Br, Cl, F, mesylate, tosylate, trifluorosulfonate (triflate);

$R^3$ is hydrogen or a protective group;

$R^4$ is hydrogen, alkyl having 1 to 5 carbon atoms, or a protective group;

$R^5$ is hydrogen, alkyl having 1 to 5 carbon atoms, or a protective group;

$Z^1$ is hydrogen, nitrogen, oxygen, or sulfur;

$Z^2$ is hydrogen, nitrogen, oxygen, or sulfur;

In preferred embodiments, the activated ester is one of the following:

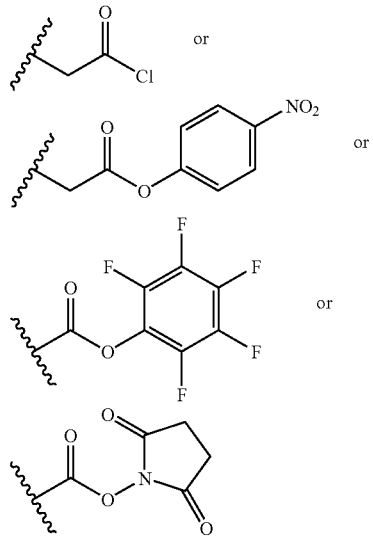

The carboxylic acid group can be preferably:

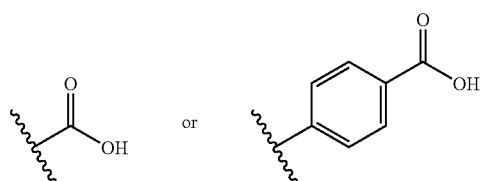

The isothiocyanato group preferably is one of the following:

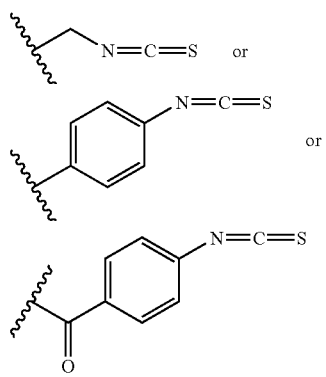

and the protective group preferably is:

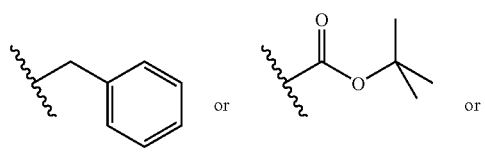

-continued

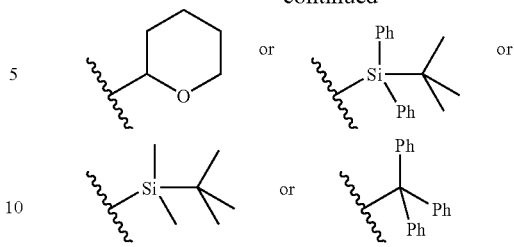

In another aspect, the present inventions also provide methods for diagnosis and treatment of receptor-positive tumors. Once linked to biologically active ligands, the conjugates can be complexed to a radioisotope metallic element and used for diagnosing or treating any appropriate receptor-positive tumors.

DETAILED DESCRIPTION OF THE INVENTION

Figure 1:
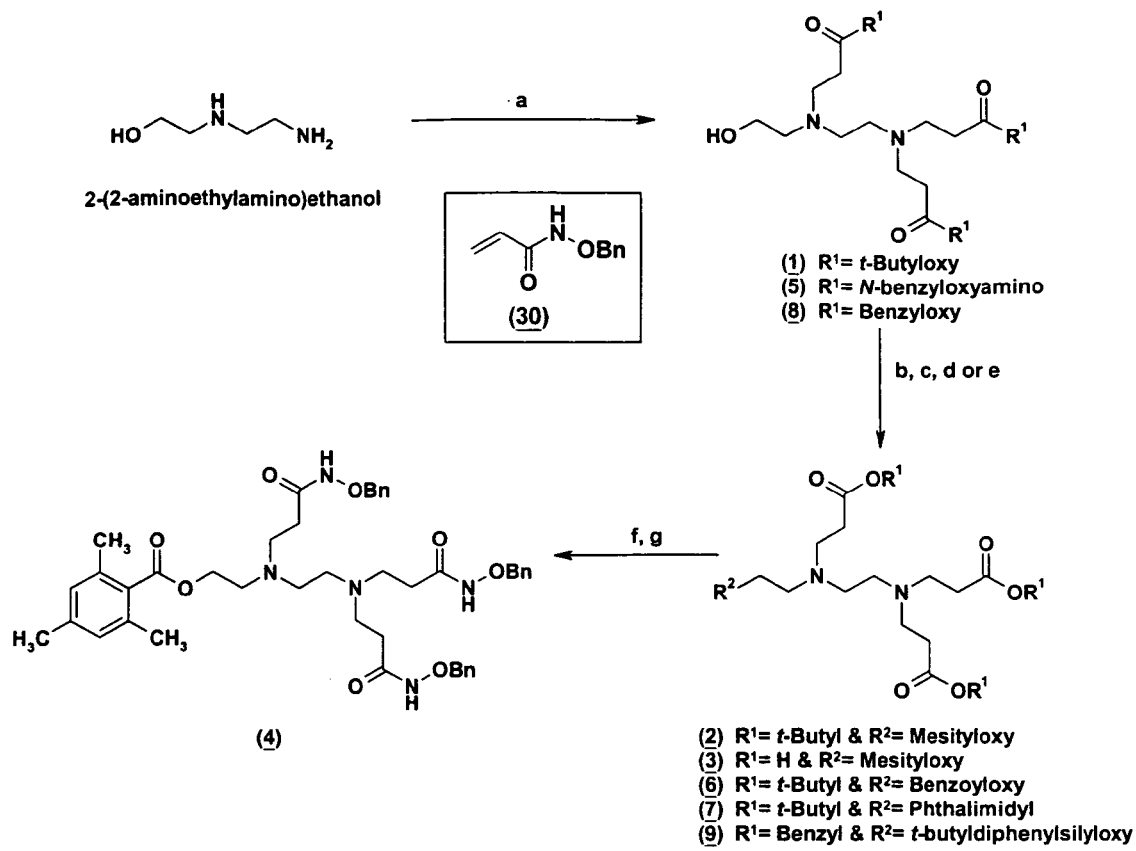
FIG. 1 provides the synthetic scheme for an ethylenediaminetrishydroxamic acid chelator (EDTHA) [a) t-Butyl acrylate or benzyl acrylate or N-benzyloxy acrylamide (30), reflux; b) 2,4,6-trimethylbenzoyl chloride, pyridine, $CH_2Cl_2$; 0° C.; c) Benzoyl chloride, pyridine, $CH_2Cl_2$, 0° C.; d) Phthalimide, diethyl azodicarboxylate, triphenyl phosphine, THF, 0° C.; e) t-Butyldiphenylsilyl chloride, triethylamine, $CH_2Cl_2$; f) 50% TFA, 2% TIPS, $CH_2Cl_2$; g) O-Benzylhydroxylamine hydrochloride, 1-(3-dimethylaminopropyl)-3-ethylcarbodiimide hydrochloride, DMAP, acetonitrile].

The chelators of the invention facilitate attachment of a metal chelating group to a peptide or protein. This attachment is effected, for example, through formation of a thiourea or amide bond. The former is usually prepared in non-aqueous media while the latter can be prepared under aqueous or non-aqueous conditions.

The multidentate chelators of the invention include two or more hydroxamic acid functionalities, and possess an attachment group that will enable linking to biologically active ligands. Such chelators satisfy all of the basic requirements to have a high affinity for metal elements such as, for example, indium, gallium, iron, and gadolinium.

The compounds of the invention can be bound to a wide variety of peptides and proteins. In one preferred embodiment, the peptides or proteins to be used include peptidomimetics containing an amino group. Among such preferred peptidomimetics are, for example, natural and synthetic somatostatin and analogues, atrial natriuretic factor peptides, fibrin binding domain peptides, monoclonal antibodies or fragments thereof, F(ab)$_2$, Fab, Fv regions, oxytocin, substance P, and vasopressin.

Preferred compounds according to the invention include radioisotopes of any detectable element. A "detectable element" as used herein is defined as any element, preferably a metal ion, that exhibits a property detectable in therapeutic or in vivo diagnostic techniques. For example, a metal ion that emits detectable radiation or a metal ion that is capable of influencing NMR relaxation properties, and that is capable of forming a conjugate or complex with the described hydroxamic acid-based chelators. Suitable detectable metal ions as used herein include, for example, heavy elements or rare earth ions such as the paramagnetic ions, $Gd^{3+}$, $Fe^{3+}$, $Mn^{2+}$ and $Cr^{2+}$. By way of example, fluorescent metal ions, such as $Eu^{3+}$, and radionuclides, such as γ-emitting radionuclides, β-emitting radionuclides, α-emitting radionuclides, and positron-emitting radionuclides. Preferred radioisotopes according to the invention are those of gallium or indium, such as $^{67}Ga$, $^{68}Ga$, or $^{111}In$.

The reaction between the chelator-peptide (or chelator-protein) conjugate and the detectable element is carried out using known methods, and preferably are performed at a pH at which the peptide or protein is stable. In one method, a complex may be formed between the chelator and a detectable element prior to coupling with the peptide or protein. In another method, a chelator is complexed first with a non-detectable metal ion and then with a peptide or protein. The non-detectable metal ion may subsequently be replaced by the desired detectable element via a transmetallation process.

The term "alkyl" as used herein refers to substituted and unsubstituted straight chain and branched hydrocarbons, particularly those having 1-20 (preferably 1-10) carbon atoms.

The term "protective group" according to the invention, includes, but is not limited to, tert-butoxycarbonyl, benzyloxycarbonyl, mesityl (2,4,6-trimethylbenzoyl)ester, benzoyl ester, tert-butyldiphenylsilyl ether, triphenylmethyl (trityl; Tr), S-tert-butyl, S-p-butyl, S-p-nitrobenzyl, and S-p-methoxy-benzyl, and phthalimido groups (see e.g., Greene and Wuts, *Protective Groups in Organic Synthesis*, 2$^{nd}$ edition, John Wiley & Sons, New York, 1991).

The term "chelator" as referenced herein refers to any organic compound containing two or more donor atoms spatially situated so as to form coordinate bonds with the same metal atom. Chelators, as referred to herein, are "multidentate", which is defined as having multiple donor atoms available for simultaneous complexing with a metal atom.

The term "active group" refers to groups that can be easily transformed, substituted or that have good leaving properties. Preferred active groups include amine, activated esters (i.e., esters that bear an electron-withdrawing group to facilitate its substitution), carboxylic acids, alkyl isothiocyanates, and aromatic isothiocyanates.

The term "animal" as referenced herein, includes all mammals, and preferably, humans.

The term "protein" as referenced herein, refers to a linear polymer of amino acids linked together and usually containing at least 50 amino acid residues. The term "peptide" as referenced herein, refers to a small polymer in which the amino acids are connected by peptide bonds, and usually containing fewer than 50 amino acid residues.

The term "complex" as referenced herein, refers to the combination of a chelator with a radioisotope or a chelator attached to a radioisotope and a peptide or protein.

Representative techniques for preparing compounds according to the invention are shown in the figures. FIG. 1, for example, shows a synthetic scheme for an ethylenediaminetrishydroxamic acid chelator (EDTHA) in which 2-(2-aminoethylamino)ethanol was treated with tert-butyl acrylate and then heated at reflux to produce N,N,N'-tris[2-(tert-butoxycarbonylethyl)]-2-(2-aminoethylamino)ethanol (1).

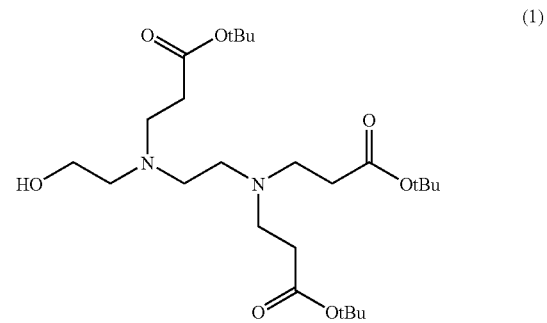

(1)

Pyridine was added. The mixture was solubilized in dry methylene chloride and cooled to 0° C. in an ice bath and a solution of 2,4,6-trimethylbenzoyl chloride. Next, dry dichloromethane was added. The resulting product was N-[2-(2',4',6'-trimethyl-phenylcarbonyloxy)ethyl],N,N,N'-tris[2-(tert-butoxycarbonyl)ethyl]-1,2-ethylenediamine (2).

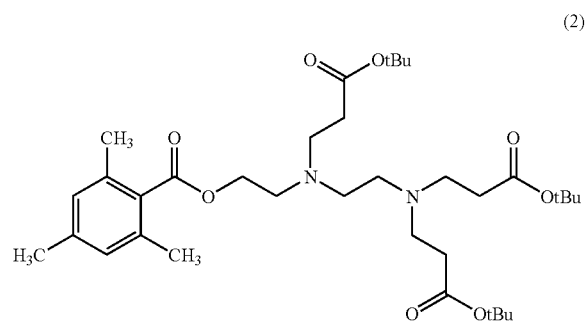

(2)

Trifluoroacetic acid was added to a solution of tributyl ester (2) in dry dichloromethane.

The residue was triturated with benzene and the solvent was removed under vacuum. Hydrochloric acid was added to the residue and the volatile substances were removed after stirring. The residual solid was dried by trituration with benzene and the solid was filtered and dried under vacuum.

N-[2-(2',4',6'-trimethylphenylcarbonyloxy)ethyl], N,N,N'-tris[2-(tert-butoxycarbonyl)ethyl]-1,2-ethylenediamine (3) dihydrochloride was produced.

was heated at reflux. The product was N,N,N'-tris[2-(benzyloxy-aminocarbonylethyl)]-2-(2-aminoethylamino)ethanol (5).

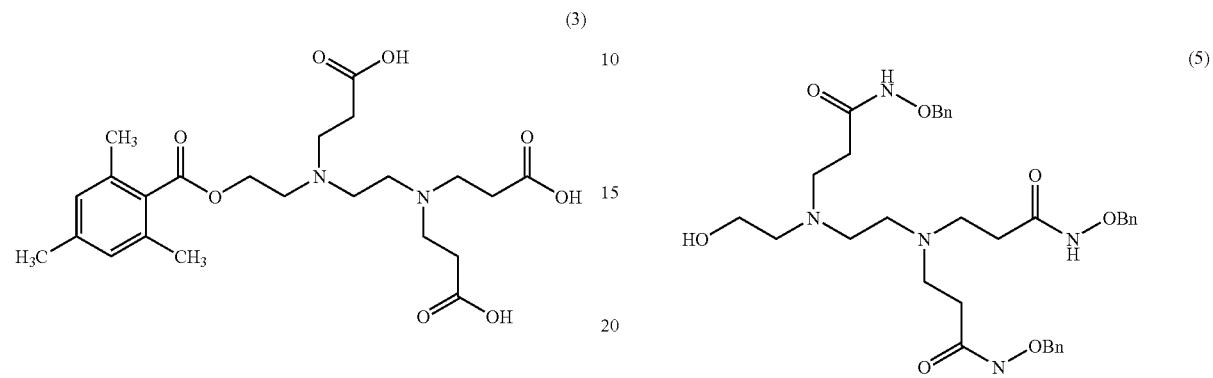

In a subsequent step, trifluoroacetic acid and trisisopropylsilane were added to a solution of N-[2-(2',4',6'-trimethylphenylcarbonyloxy)ethyl],N,N,N'-tris[2-(tert-butoxycarbonyl)ethyl]-1,2-ethylenediamine (2) in dry dichloromethane. The mixture was stirred and the volatile substances were removed under reduced pressure. The residue was treated with 0.1N hydrochloric acid and then concentrated under vacuum. 1-(3-Dimethylaminopropyl)-3-ethylcarbodiimide hydrochloride and 4-(N,N-dimethylamino)pyridine were added to a mixture of N-[2-(2',4',6'-trimethylphenylcarbonyl-oxy)ethyl],N,N,N'-tris[2-(hydroxycarbonylethyl)]-1,2-ethylenediamine (3) hydrochloride and O-benzyl hydroxylamine hydrochloride in acetonitrile. Another quantity of 4-(N,N-dimethylamino)pyridine was added. N-[2-(2',4',6'-trimethylphenylcarbonyloxy)ethyl],N,N,N'-tris[2-(benzyloxyaminocarbonyl)ethyl]-1,2-ethylenediamine (4) was produced.

The second reactive step involved adding pyridine to a cooled solution of tert-butyl hydroxytrispropionate dissolved in dichloromethane. The mixture was stirred at 0° C. followed by the addition of benzoyl chloride. Later purification using dichloromethane/ethyl acetate/N,N-diisopropyl ethylamine produced N-[2-(benzoyloxy)ethyl],N,N,N'-tris[2-(tert-butoxycarbonyl-ethyl)]-1,2-ethylenediamine (6).

Another pathway for producing the third structure disclosed in the synthetic scheme involved adding diethyl azodicarboxylate to a cooled solution of N,N,N'-tris[2-(tert-butoxycarbonylethyl)]-2-(2-aminoethylamino)ethanol (1), phthalimide, and triphenylphosphine dissolved in dry tetrahydrofuran. Later purification produced N-[2-phthalimidoethyl],N,N,N'-tris[2-tert-butoxycarbonylethyl]-1,2-ethylenediamine (7).

An alternative initial step involved adding 2-(2-aminoethylamino)ethanol to a solution of N-benzyloxy acrylamide (30) solubilized in tetrahydrofuran. The resulting solution Yet another initial reactive step in the synthetic scheme discloses a solution of 2-(2-aminoethylamino)ethanol dissolved in benzyl acrylate heated at reflux. Purification produced the desired material, N,N,N'-tris[2-(benzyloxycarbonyl)ethyl]-2-(2-amino-ethylamino)ethanol (8).

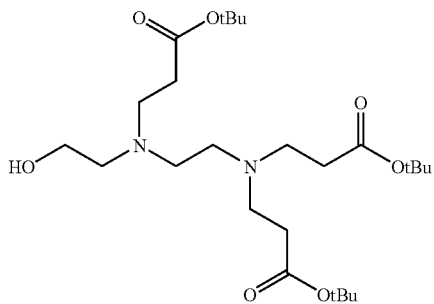
(8)

The second reactive step in which compound (8) becomes compound (9) involves adding dry dichloromethane to dissolve N,N,N'-tris[2-(benzyloxycarbonyl)ethyl]-2-(2-amino-ethylamino)ethanol (8). Triethylamine and 4-(N,N-dimethylamino)pyridine were added and stirred before adding tert-butylchlorodiphenylsilane. Purification by flash chromatography using dichloromethane and ethyl acetate produced the desired compound, N-[2-(tert-butyldiphenyl-silyloxy)ethyl],N,N,N'-tris[2-(benzyloxycarbonyl)ethyl]-1,2-ethylenediamine (9).

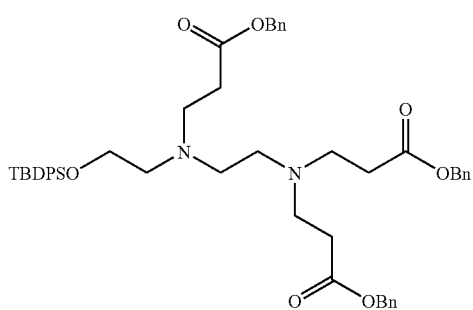
(9)

Figure 2:
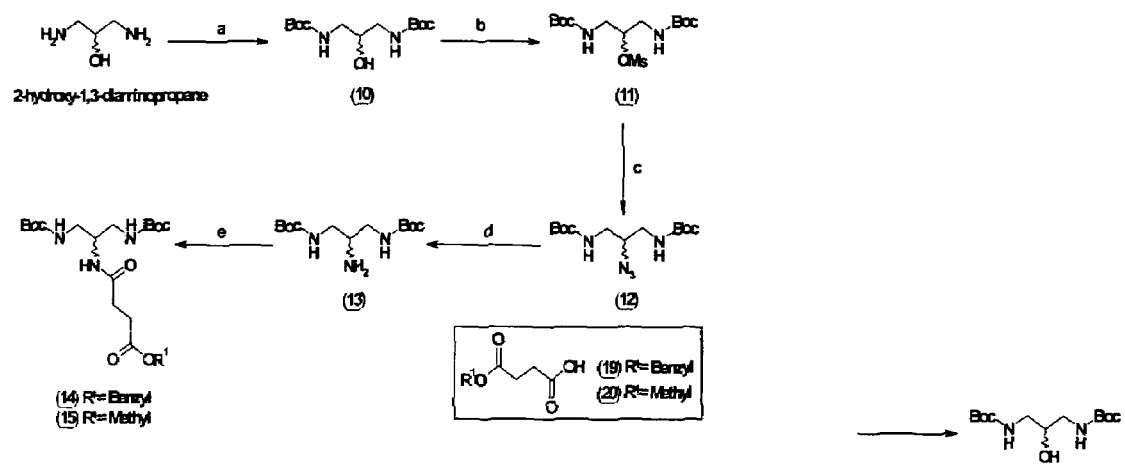
FIG. 2 provides a synthetic scheme for di-Boc 1,2,3-trisaminopropane based chelator [a) $Boc_2O$, $Na_2CO_3$, $H_2O$, Dioxane, 0° C.; b) MsCl, $Et_3N$, $CH_2Cl_2$, 0° C.; c) $NaN_3$, DMF, 70° C.; d) $H_2$, 10% Pd/C, MeOH, 50 psi; e) compound 19 or compound 20, 1M DCC, HOBT, DIPEA, EtOAc, 0° C.].

FIG. 2 shows a synthetic scheme for trisaminopropane tetrapropiohydroxamic acid chelator (TPTHA). A solution of 2-hydroxy-1,3-diaminopropane in water was cooled to 0° C. A mixture of tert-butyl dicarbonate in 1,4-dioxane was added. Sodium carbonate was added. The solvent was eliminated under reduced pressure. Recrystalization of the residue with a mixture of diethyl ether and hexane produced the desired $N^1,N^3$-bis(tert-butoxycarbonyl)-1,3-diamino-2-propanol (10).

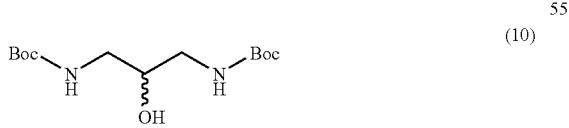
(10)

A mixture of 1,3-diamino-2-propanol and triethylamine was cooled to 0° C. in an ice bath. Methanesulfonyl chloride was added. Water was added and the two layers were separated. The aqueous layer was extracted with dichloromethane. The end product was $N^1,N^3$-bis(tert-butoxycarbonyl)-2-methanesulfonyloxy-1,3-diaminopropane (11).

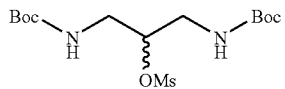
(11)

Sodium azide was added to a solution of the di-(tert-butoxycarbonylamino)mesylate (11) in N,N-dimethylformamide. $N^1,N^3$-bis-(tert-butoxycarbonyl)-2-azido-1,3-diaminopropane (12) was produced.

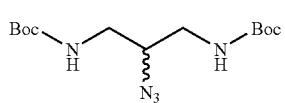
(12)

A solution of $N^1,N^3$-bis-(tert-butoxycarbonyl)-2-azido-1,3-diaminopropane (12) in methanol was poured into a Parr hydrogenation bottle. A palladium catalyst was added. The mixture was degassed followed by the introduction of a hydrogen atmosphere (50 psi). The reaction was shaken and the hydrogen was removed in vacuo. The catalyst was then filtered off over celite and the filtrate was concentrated by rotatory evaporation to produce $N^1,N^3$-bis(tert-butoxycarbonyl)-1,2,3-triaminopropane (13) as a solid.

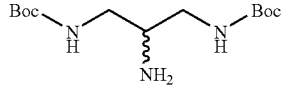
(13)

Mono-benzyl succinate (19), 1-hydroxybenzotriazole hydrate, N,N-diisopropyl-ethylamine, and dry ethyl acetate were mixed and cooled to 0° C. with an ice bath followed by the addition of 1M N,N'-dicyclohexylcarbodiimide in dichloromethane solution. The mixture was stirred under an atmosphere of argon before adding a solution of $N^1,N^3$-bis(tert-butoxycarbonyl)-1,2,3-triaminopropane dissolved in dry ethyl acetate. The desired product was produced, benzyl N-[2-[1,3-bis(tert-butoxycarbonyl-amino)]propyl]succinamate (14).

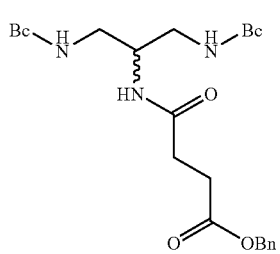
(14)

Another pathway for producing the desired final product is by cooling mono-methyl succinate (20), 1-hydroxybenzotriazole hydrate, N,N-diisopropylethylamine, and dry ethyl acetate to 0° C. with an ice bath followed by adding 1M 1,3-dicyclo-hexylcarbodiimide in dichloromethane. The mixture was stirred under an atmosphere of argon before adding a solution of $N^1,N^3$-bis-(tert-butoxycarbonyl)-1,2,3- triaminopropane dissolved in dry ethyl acetate. Purification produced methyl N-[2-[1,3-bis(tert-butoxycarbonylamino)]propyl]succinamate (15).

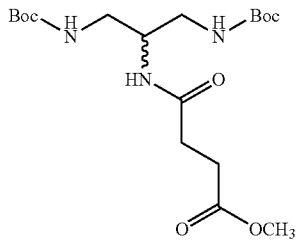

(15)

Figure 3:
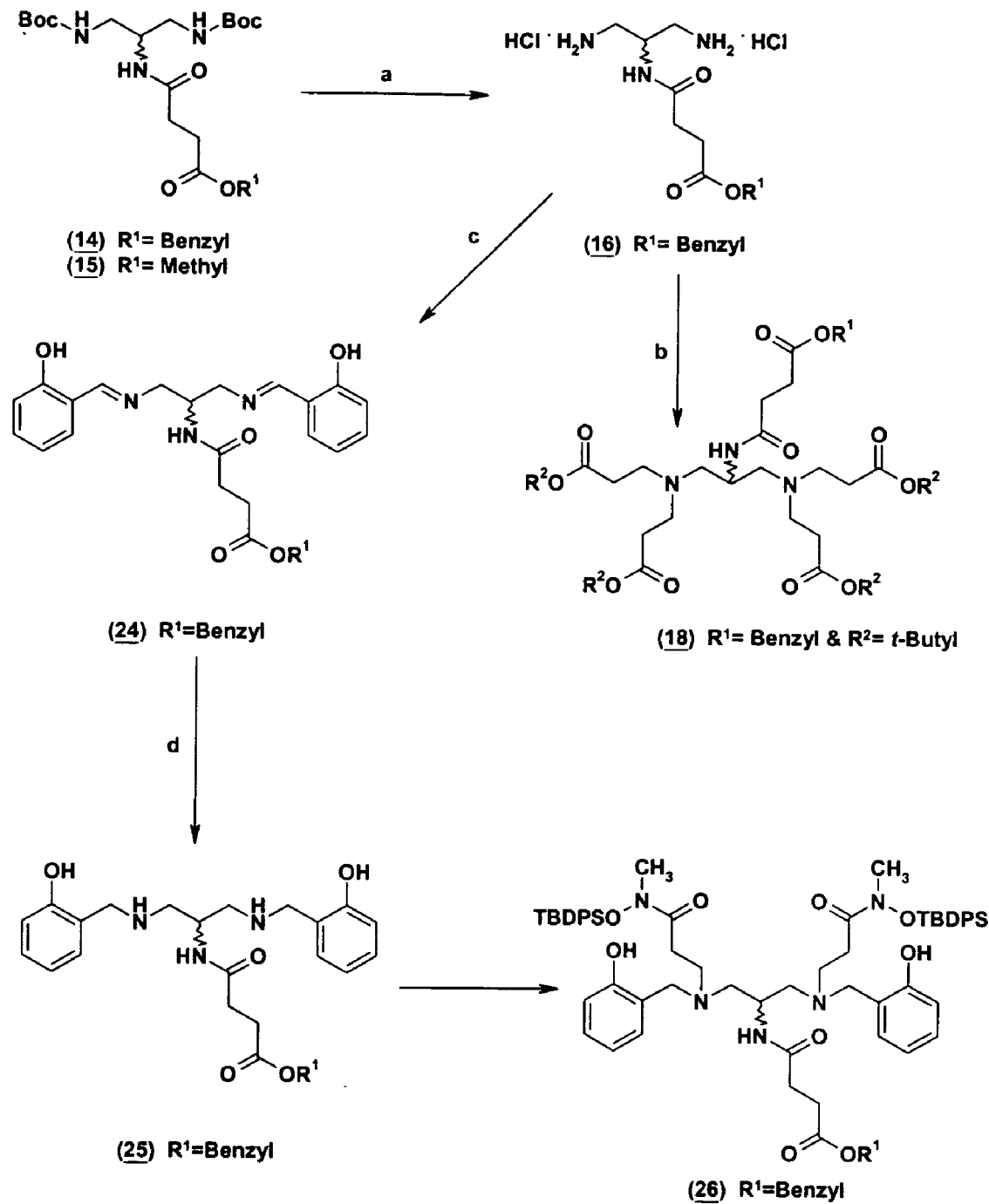
FIG. 3 provides a synthetic scheme for a 1,2,3-trisaminopropane tetrapropio-hydroxamic acid chelator (TPTHA) and a 1,2,3-trisaminopropane bis-[2'-hydroxybenzyl]dihydroxamic acid chelator (HBTDHA) [a) 1M HCl/EtOAc; b) t-Butyl acrylate; c) Salicylaldehyde, $Et_3N$, benzene, reflux, —$H_2O$; d) $H_2$, 10% Pd/C, methanol].

FIG. 3 provides a synthetic scheme for 1,2,3-trisaminopropane based chelators (TPTHA). The synthetic scheme begins with Benzyl N-[2-[1',3'-bis(tert-butyloxycarbonylamino)]propyl]succinamate (14) was treated with a 1.0M hydrochloric acid solution in ethyl acetate. Hydrolysis produced benzyl N-(1',3'-diamino-2'-propyl)succinamate dihydrochloride (16).

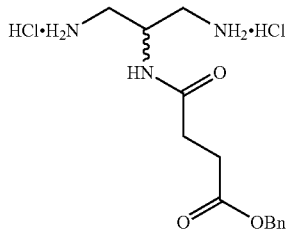

(16)

A mixture of 1,3-diamino-2-propanol and tert-butyl acrylate was heated at reflux with stirring, and under an atmosphere of argon. Purification produced the desired product, $N^1,N^1,N^3,N^3$-tetra[2'-(tert-butoxycarbonyl)ethyl]-1,3-diamino-2-propanol (17).

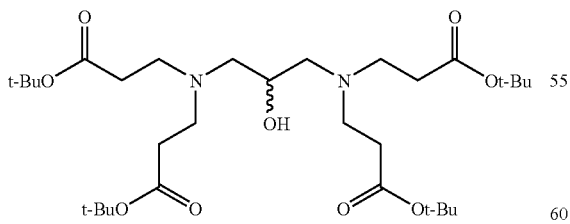

(17)

N,N-Diisopropylethylamine was added to a suspension of benzyl N-(1',3'-diamino-2'-propyl)succinamate dihydrochloride (16) in dry tetrahydrofuran. Tert-butyl acrylate was then added and the solution was heated at reflux. The resulting product was benzyl N-[2-[$N^1,N^1,N^3,N^3$-tetra[2'-(tert-butoxycarbonyl)ethyl]-1,3-diaminopropyl]]succinamate (18).

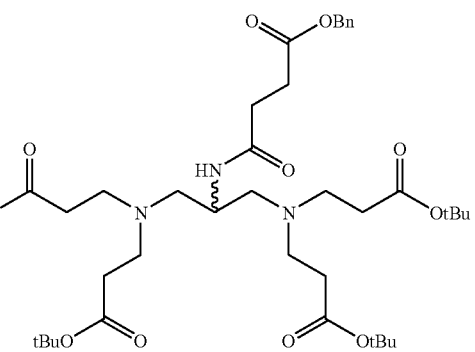

(18)

A mixture of succinic anhydride and benzyl alcohol was shaken while heated at reflux with a steam bath until all of the succinic anhydride was dissolved. The excess of benzyl alcohol was removed under reduced pressure and the residue was cooled with an ice bath. The precipitate was filtered off and triturated with water. The solid was dried under vacuum until constant weight. Thus, monobenzyl succinate (19) was recovered.

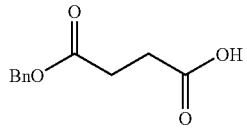

19

A mixture of succinic anhydride and dry methanol was shaken while heated at reflux with a steam bath until all the succinic anhydride was dissolved. The excess of methanol was removed under reduced pressure and the residue was cooled with an ice bath. The precipitate was filtered off and triturated with water. The solid was dried under vacuum until constant weight. Thus, mono-methyl succinate (20) was recovered.

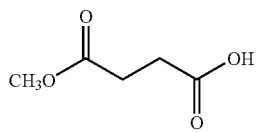

20

Synthesis of the intermediate, benzyl N-[2-[$N^1,N^3$-bis(2'-hydroxybenzylidene)]-1,3-diaminopropyl]succinamate (24), involves adding benzene, dichloromethane, and N,N-diisopropylethylamine to benzyl N-(1',3'-diamino-2'-propyl)succinamate dihydrochloride (16). Salicylaldehyde was added and the reaction mixture was heated at reflux. The resulting solid was purified by flash chromatography on silica gel using a mixture of dichloromethane and ethyl acetate. The purification produced benzyl N-[2-[$N^1,N^3$-bis(2'-hydroxybenzylidene)]-1,3-diaminopropyl]succinamate (24).

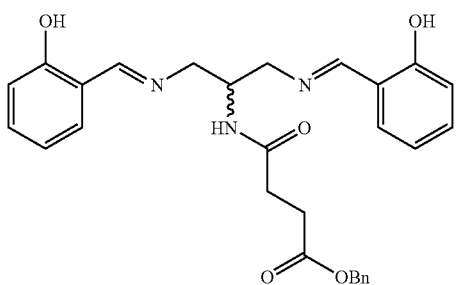
(24)

Benzyl N-[2-[$N^1,N^3$-bis(2'-hydroxybenzylidene)]-1,3-diaminopropyl]succinamate (24) was dissolved with a mixture of ethanol, tetrahydrofuran. Sodium borohydride was added. The mixture was stirred and water was added. After concentration, dichloromethane and water were added. The water solution was extracted with dichloromethane and the organic layers were combined. The solvent was evaporated and the residue was purified by flash chromatography (dichloromethane/methanol/ammonium hydroxide), producing benzyl N-[2-[$N^1,N^3$-bis(2'-hydroxybenzyl)]-1,3-diaminopropyl]succinamate (25).

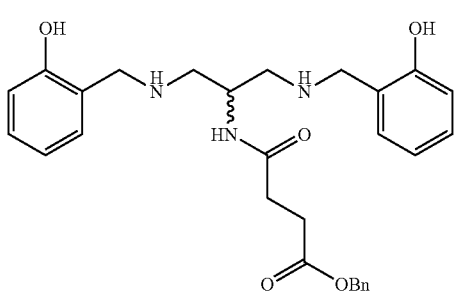
(25)

Benzyl N-[2-[$N^1,N^3$-bis(2'-hydroxybenzyl)]-$N^1,N^3$-[bis[2-[N'-methyl,N'-(ter-butyldiphenylsilyloxy)]aminocarbonyl]ethyl]]-1,3-diaminopropyl]succinamate (26) is prepared by treating benzyl bis(2'-hydroxybenzyl)diamino succinimate (25) with an excess of N-methyl,N-(tert-butyldiphenylsilyloxy)acrylamide (28) in presence of a base such as N,N-diisopropylethylamine.

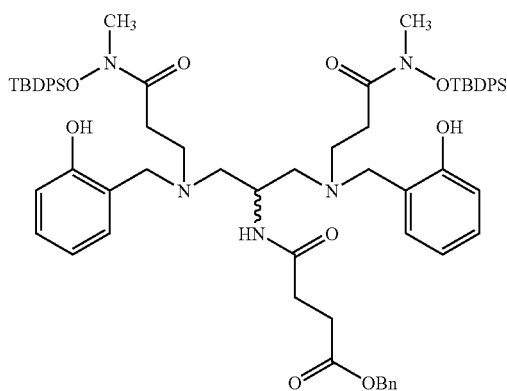
(26)

Figure 4:
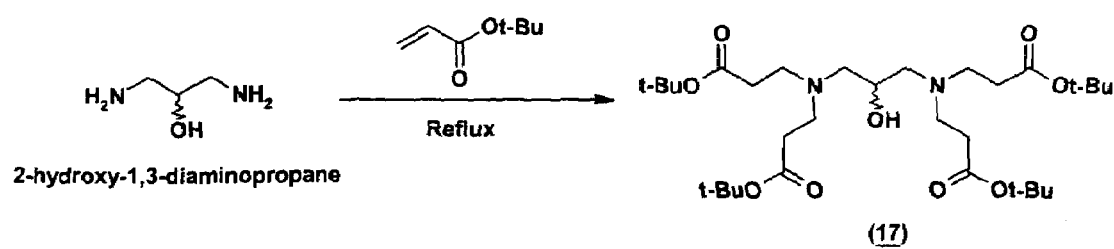
FIG. 4 provides a synthetic scheme for a 1,3-diamino-2-propanol tetrapropio-hydroxamic acid chelator (DPTHA).

FIG. 4 shows a synthetic scheme for the preparation of $N^1,N^1,N^3,N^3$-tetra[2'-(tert-butoxycarbonyl)ethyl]-1,3-diamino-2-propanol (17), a possible precursor of TPTHA. 1,3-diamino-2-propanol was treated at reflux with an excess of tert-butyl acrylate. The Michael type addition produced the desired product in excellent yield after purification by chromatography.

Figure 5:
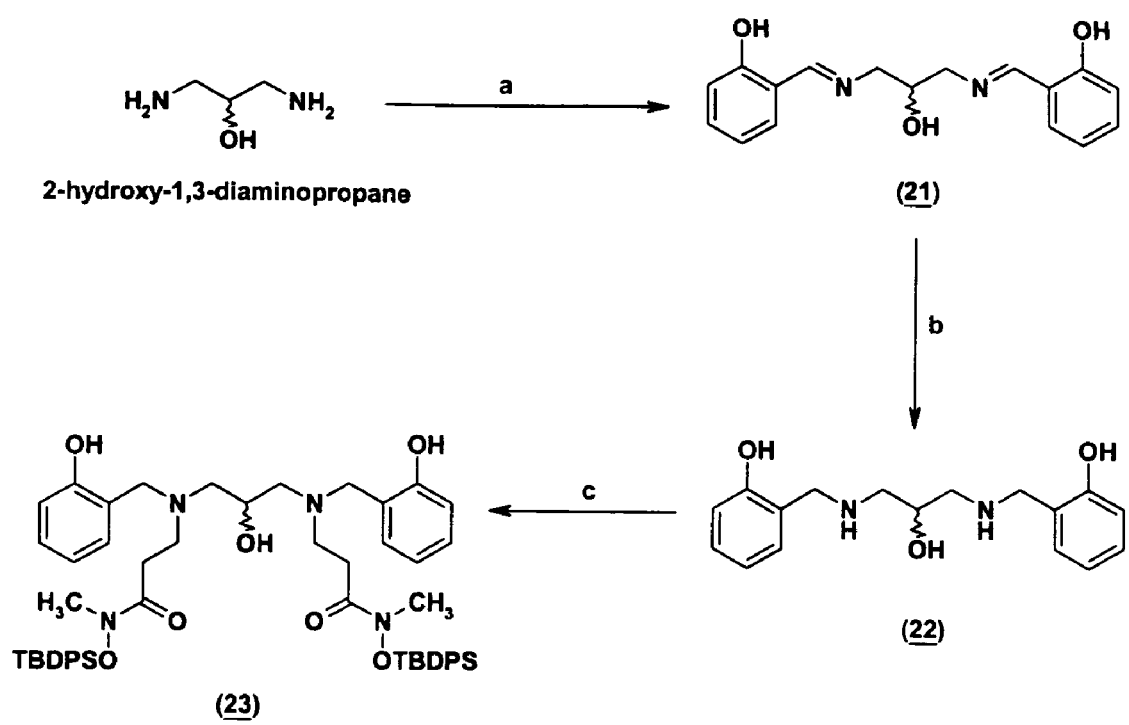
FIG. 5 provides a synthetic scheme for a 1,3-diamino-2-propanol bis-[2'-hydroxybenzyl]dihydroxamic acid chelator (HBDDHA) [a) Salicylaldehyde, benzene, reflux, —$H_2O$; b)) $H_2$, 10% Pd/C, methanol; c) compound 28, THF, reflux]
Figure 6:
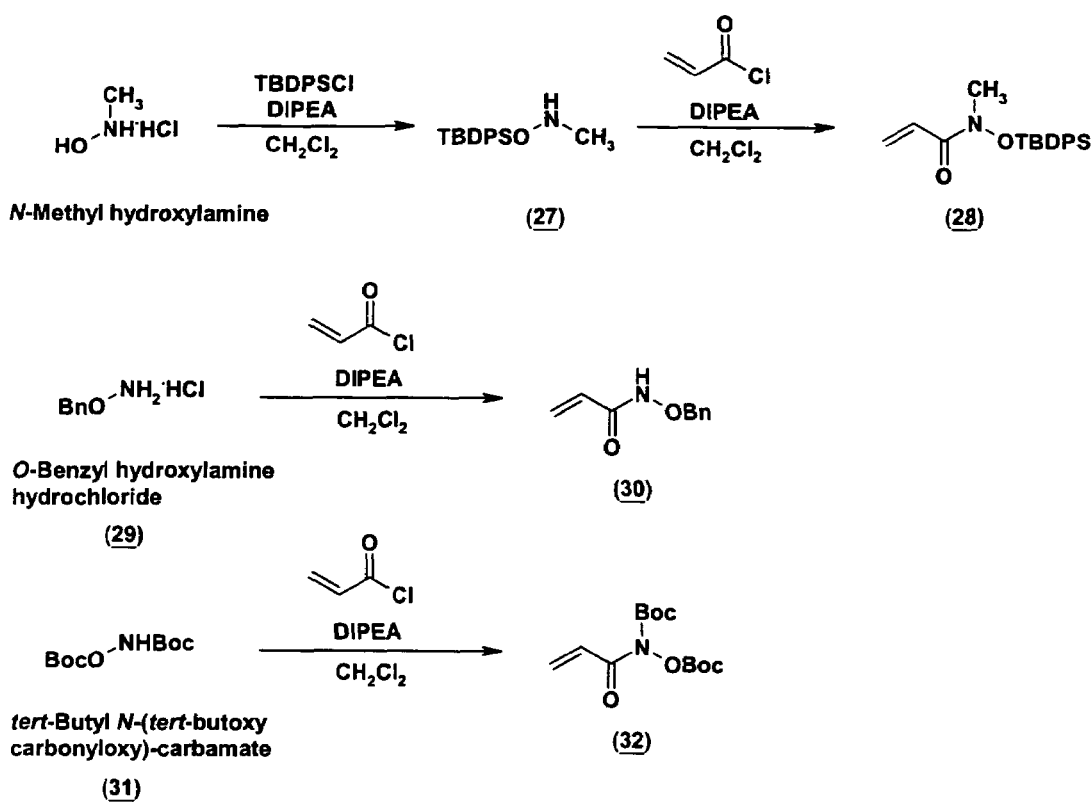
FIG. 6 provides a synthetic scheme for N-hydroxy acrylamide derivatives.

FIG. 5 shows a synthetic scheme for the synthesis of a trisaminopropane bis-[2'-hydroxybenzyl]dihydroxamic acid chelator (HBTDHA). 1,3-Diamino-2-propanol is added to a mixture of salicylaldehyde and benzene and heated to reflux. The reaction produced $N^1,N^3$-bis(2'-hydroxybenzylidene)-1,3-diamino-2-propanol (21) after drying under vacuum.

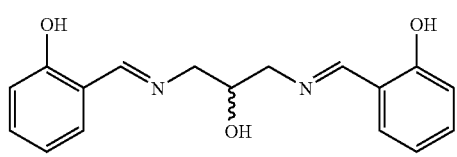
(21)

Palladium on charcoal was added to a solution of $N^1,N^3$-bis-(2'-hydroxybenzylidene)-1,3-diamino-2-propanol (21) in methanol. After degassing, filtering, concentrating and purifying, the resulting product was $N^1,N^3$-bis-(2'-hydroxybenzyl)-1,3-diamino-2-propanol (22).

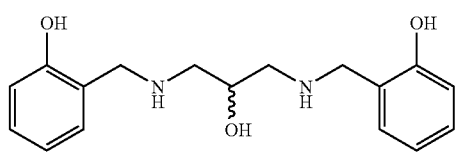
(22)

$N^1,N^3$-bis-(2'-hydroxybenzyl)-1,3-diamino-2-propanol (22) was added to a solution of N-methyl,N-(tert-butyldiphenylsilyloxy)acrylamide (28) in tetrahydrofuran and heated at reflux. After removing the volatile substances, the residue was purified by flash chromatography using a mixture of dichloromethane, methanol, and N,N-diisopropylethylamine. The solvents were eliminated from the desired fractions, producing $N^1,N^3$-[bis(2'-hydroxybenzyl)]-$N^1,N^3$-[bis[2-[N'-methyl,N'-(ter-butyldiphe-nylsilyloxy)aminocarbonyl]ethyl]]-1,3-diamino-2-propanol (23).

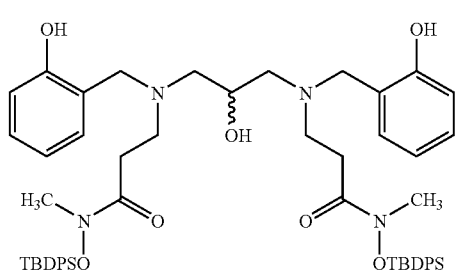
(23)

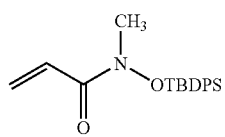
(28)

One possible synthetic scheme for hydroxylamine derivatives involves adding tert-butyldiphenylsilyl chloride and N,N-diisopropylethylamine to a suspension of N-methyl hydroxylamine hydrochloride in dry dichloromethane. The reaction mixture was stirred followed by the addition of water. The two layers were separated and the aqueous layer was extracted with methylene chloride. The organic solutions were then combined, dried with magnesium sulfate, filtered, and concentrated to dryness under reduced pressure. The resulting product was purified by liquid chromatography on silica gel using a mixture of hexane and ethyl acetate to elute the desired product. The purification process gave N-Methyl,N-(tert-butyldiphenylsilyl)hydroxylamine (27).

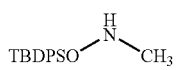

(27)

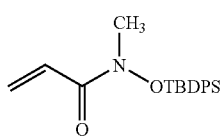

(28)

Dry dichloromethane (50 mL) was added to N-Methyl, N-(tert-butyldiphenylsilyl)hydroxylamine to dissolve the hydroxylamine derivative. N,Ndiisopropylethylamine was added. The resulting solution was stirred and cooled at 0° C. with an ice bath. Acryloyl chloride in 10 mL of dry dichloromethane was added. Then water was added and the two layers were separated. The organic layer was washed with 10% ammonium chloride, saturated bicarbonate solution, and brine. The organic solution was then dried with magnesium sulfate, filtered, and the solvent evaporated under reduced pressure. The crude product was purified by flash chromatography (silica gel) using a mixture of hexane and ethyl acetate to elute the compound. The purification produced N-Methyl,N-(tert-butyldiphenylsilyloxy)acrylamide (28).

Two other useful hydroxylamine derivatives are O-benzylhydroxylamine (29), and tert-butyl N-(tert-butoxycarbonyloxy)carbamate (31), both of which are commercially available and can be obtained from Sigma-Aldrich Canada Ltd. (Oakville, Ontario).

A solution of acryloyl chloride dissolved in dry dichloromethane was cooled at 0° C. with an ice bath. A mixture of O-benzyl hydroxylamine hydrochloride (29) and N,N-diisopropylethylaamine in dry dichloromethane was added. Water was added and the layers were separated. The organic solution was washed with diluted hydrochloric acid, a saturated sodium bicarbonate solution, water, and brine. The organic layer was dried over magnesium sulfate, filtered, and the solvent removed under reduced pressure. The residue was purified by flash chromatography using a mixture of hexane and ethyl acetate. The purification gave N-benzyloxyacrylamide (30).

(29)

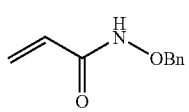

(30)

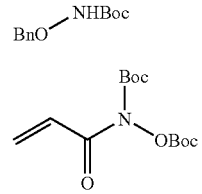

(31)

(32)

A solution of acryloyl chloride dissolved in dry dichloromethane was cooled at 0° C. with an ice bath. A mixture of tert-butyl N-(tert-butoxycarbonyloxy)carbamate (31) and N,N-diisopropylethylamine in dry dichloromethane was added. Water was added after 16 hours of reaction and the layers were separated. The organic solution was washed with diluted hydrochloric acid, a saturated sodium bicarbonate solution, water, and brine. The organic layer was dried over magnesium sulfate, filtered, and the solvent removed under reduced pressure. The residue was purified by flash chromatography using a mixture of hexane and ethyl acetate (90:10). The purification gave N-(tert-butoxycarbonyl), N-(tert-butoxycarbonyloxy)acrylamide (32).

The compounds of the invention are useful, for example, as diagnostic imaging agents to visualize particular peptides or receptor-positive tumors and metastases when complexed, for example, with a paramagnetic, a γ-emitting metal ion or a positron-emitting radionuclide. The compounds of the present invention are also useful as therapeutic radiopharrnaceuticals for the treatment in vivo of peptide receptor-positive tumors and metastases when complexed with a β-emitting, or α-emitting radionuclide, as indicated by standard tests. As will be recognized by those skilled in the art, the organ or system to be radioimaged generally dictates the radioisotope that is chosen for use with the compounds of the invention.

The compounds of the invention can be used, for example, as diagnostic or therapeutic agents, as research reagents or in kits. The compounds of the invention can be used in pharmaceutical compositions by including a suitable pharmaceutically acceptable diluent or carrier. The compositions may be formulated in pharmaceutical compositions, which may include carriers, thickeners, diluents, buffers, preservatives, surface active agents and the like, in addition to the compounds.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable. Formulations for parenteral administration may include sterile aqueous solutions that may also contain buffers, diluents and other suitable additives.

The compounds of the invention, when used as imaging agents, may be administered parenterally, preferably intravenously in the form of injectable solutions or suspensions and in the form of a single injection. The appropriate dosage will vary depending upon considerations that are well known by one of ordinary skill in the art, such as the precise radioisotope and the type of detectable element used, e.g., the radionuclide. A dose would be considered suitable if it permits imaging by photoscanning procedures known in the art. It may advantageously be administered in a dose having a radioactivity of from 0.1 to 50 mCi, preferably 0.1 to 30 mCi, more preferably 0.1 to 20 mCi. In one embodiment, an indicated dosage range may be of from 1 to 200 μg of the compound labeled with 0.1 to 50 mCi and preferably 0.1 to 30 mCi, γ-emitting radionuclide, depending on the γ-emitting radionuclide used. In another preferred embodiment, the indicated dosage range may be of from 1 to 200 ug of compound labeled with 3 to 15 mCi γ-emitting radionuclide.

Enrichment in the tumorigenic sites with the compounds of the invention can be followed by the corresponding imaging techniques, such as nuclear medicine imaging instrumentation, including a scanner, planar or rotating γ-camera, each preferably computer assisted, a PET scanner (Positron Emission Tomography) or MRI equipment.

Products containing the compounds of the invention can be used for in vivo treatment of peptide receptor-positive tumors and metastases in a subject in need of such a treatment by administering to said subject a therapeutically effective amount of the product. Dosages employed in practicing the therapeutic method of the present invention will vary depending on factors with which one of ordinary skill in the art is familiar, such as the particular condition to be treated, the volume of the tumor, the particular product employed, the half-life of the product in the tumor, and the therapy desired. In general, the dose is calculated on the basis of radioactivity distribution to each organ and on the observed target uptake. For example, the product may be administered at a daily dosage range having a radioactivity of from 0.1 to 3 mCi/kg body weight. In one embodiment the daily dosage range is 1 to 3 mCi, preferably 1 to 1.5 mCi/kg body weight. In another embodiment, the indicated daily dosage range is of from 1 to 200 μg radioisotope labeled with 0.1 to 3 mCi/kg body weight. In yet another embodiment, the indicated daily dosage range is from 0.1 to 1.5 Ci/kg body weight α- or β-emitting radionuclide. Administration can be effected in divided doses up to 4 times a day.

The pharmaceutical compositions may be administered by any conventional route, depending on whether local or systemic treatment is desired, and on the area to be treated. Administration can be done topically, including ophthalmically, vaginally, rectally, intranasally, orally by inhalation, or parenterally, for example, by intravenous drip or subcutaneous, intraperitoneal or intramuscular injection. In particular, the compositions can be administered parenterally in the form of injectable solutions or suspensions. The pharmaceutical composition may also be administered advantageously by infusion for, for example, 30 to 60 minutes. Depending on the site of the tumor, the compounds are administered as close as possible to the tumor site, for example, by means of a catheter. The mode of administration selected may depend on the dissociation rate of the product used and the excretion rate.

The compositions of the present invention can be administered in free form or in pharmaceutically acceptable form, such as salts which may be prepared in conventional manner and exhibit the same order of activity as the free compounds.

The compounds for use in the method of the present invention preferably are prepared shortly before being administered to a subject. More specifically, radiolabeling with the desired detectable metal ion, particularly the desired γ-, β-, or α-radionuclide, may be performed shortly before the administration. Thus prepared, they are suitable for imaging or treating tumors, including, but not limited to pituitary, gastroenteropancreatic, central nervous system, breast, prostatic, ovarian or colonic tumors, small cell lung cancer, paragangliomas, neuroblastomas, pheochromocytomas, medullary thyroid carcinomas, myelomas, and metastases thereof, as well as lymphomas.

Compositions according to the invention can be presented, for example, in a separate package with instructions for mixing the chelator-peptide product with the metal ion and for the administration of the resulting radiolabeled product. Another means for presenting the compounds is in twin-pack form, that is, as a single package containing separate unit dosages of the radioisotope and the detectable metal ion with instructions for mixing them and for administration of the product. A diluent or carrier may be present in the unit dosage forms.

A preferred use of the polyhydroxamic acid-based chelators of this invention is in coupling to a somatostatin receptor-binding peptide. One such peptide is the hexapeptide having formula:

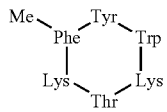

wherein Phe, Tyr, Trp, Lys, Thr, and Lys are the usual amino acids. This and other suitable peptides are disclosed in *Tetrahedron Letters*, 32 (36), 4675-4678 (1991). Such cyclic hexapeptides can be linked via an isothiocyanato or carboxylate moiety to one of the polyhydroxamic acid-based compounds of the invention, and then optionally labeled with $^{67}$Ga.

Additional objects, advantages, and novel features of this invention will become apparent to those skilled in the art upon examination of the following examples thereof, which are not intended to be limiting.

EXAMPLE 1

Preparation of the Ethylenediamine Trishydroxamic Acid Chelators (EDTHA)

Preparation of the ethylenediamine trishydroxamic acid chelators (EDTHA) of the present invention can be achieved in two similar approaches. Both pathways require a Michael addition of 2-(2-aminoethylamino)ethanol on acrylic acid derivatives. In the indirect method, the derivatives used are tert-butyl or benzyl esters of acrylic acid. This reaction typically leads to the desired intermediate without producing a significant amount of by-product. Afterwards, the primary alcohol of the obtained adducts (1 or 8 is then protected with one of the following protective groups: mesityl (2,4,6-trimethylbenzoyl)ester, benzoyl ester, tert-butyldiphenylsilyl ether or transformed into a phthalimido group. The former protective group being more resistant to the reaction conditions encountered in the formation of the hydroxamate functions. The benzyl hydroxamates can be deprotected by a mild hydrogenolysis to give a new ethylenediaminetrishydroxamic acid chelator. On the other hand, an acrylhydroxamate derivative, (such as compounds 28, 30 or 32), is used in the more direct approach.

A series of modifications on the 2-hydroxyethyl side chain of the obtained adducts have to be achieved to allow the attachment of the chelators to a substrate peptide or protein.

The next two types of polyhydroxamic acid-based chelators (TPTHA and HBTDHA) have the common N-[2-(1,3-diaminopropanyl)]succinamic acid skeleton which possesses the necessary alkyl extension that will act subsequently as a linker between the chelator and the peptide or protein. The synthesis of this key intermediate is depicted in FIG. 2.

In this synthesis, 1,3-diamino-2-propanol undergoes a series of five chemical transformations that produces the desired methyl or benzyl N-[2-(1,3-di(tert-butoxycarbonylamino)propanyl)]succinamates (14 and 15) in approximate overall yield of 53% and 57%, respectively.

Removal of the two tert-butoxycarbonyl protective groups on compound (14) provides benzyl N-[2-(1,3-diaminopropanyl)]succinamate (16) which can be either condensed with salicylaldehyde to give the bis-(2-hydroxybenzylidene)derivative (24) or added via a Michael type reaction on an acrylic or a acrylhydroxamate ester to produce a tetrapropionate or tetrapropiohydroxamatederivative. Subsequent reduction of the imine functions on the bis-(2-hydroxybenzylidene) derivative (24) produced a compound that contains two secondary amines that can react with acrylic acid derivatives to ultimately produce the third class of polyhydroxamic acid-based chelators.

Another approach, described in FIG. 5 produces the third class of disclosed chelators and consists of introducing the required functional groups that are responsible for the chelation of metal ions prior to the formation of the side chain that will provide the necessary linker moiety to attach the chelator to a peptide or protein. Protection of the phenolic functions must be performed before carrying out the rest of the reactions that will lead to the desired bifunctional chelator.

Unless otherwise stated, all reactions were carried out in flame-dried flasks at room temperature under an argon atmosphere with magnetic stirring. After extractions, organic solvents were dried over magnesium sulfate ($MgSO_4$), filtered, and removed under reduced pressure on a rotary evaporator. HPLC grade solvents, starting materials, reagents, and deuterated solvents were purchased from Sigma-Aldrich Canada Ltd. (Oakville, On.) and used without further purification.

$^1$H NMR spectra were obtained on Bruker NMR instruments (Models AMX-300, ARX-400, AM-500, and DMX-600; University of Montreal, Quebec). Samples were dissolved in $CDCl_3$, $CD_3OD$, DMSO-$d_6$, or $D_2O$ and chemical shifts were reported as δ values with the solvent or tetramethylsilane resonance as the internal standard. S (singlet), bs (broad signal), d (doublet), t (triplet), q (quartet), qn (quintuplet), and m (multiplet) define the signal multiplicity (app.=apparent). $^{13}$C NMR were spectra were recorded on a Bruker ARX-400 spectrometer at 100 MHz (and the degree of substitution of each carbon atom was determined by complete decoupling and DEPT composed 135° pulsed sequence experiments). For some of the more complex $^{13}$C NMR spectrum, the carbon and proton signals were assigned by heterocorrelation experiments.

Infrared (IR) spectra (solution cells (sodium chloride)-$CDCl_3$ as solvent or neat (sodium chloride disk)) were recorded on a Perkin-Elmer FTIR 1600 infrared spectrophotometer. Melting points were determined on a Thomas Hoover capillary melting point apparatus and are uncorrected. Mass spectra (MS) were recorded either in the DCI (methane gas), EI (Electron Ionisation) or ES (Electrospray) mode using either a Finnigan TSQ 4500 mass spectrometer (DCI, EI) or Finnigan TSQ 700 mass spectrometer (ES) and were recorded by Oneida Research Services, Inc. (Whitesboro, N.Y.). Flash chromatography was performed essentially as described in the literature (W. Clark Still et al.) using Merck silica gel 60 (230-400 mesh) as stationary phase with the use of the following solvents: methanol, methylene chloride (dichloromethane), hexane, ethyl acetate, diethyl ether, and ammonium hydroxide ($NH_4OH$). Instant thin layer chromatography (ITLC) was performed using Gelman's Silica gel (SG) chromatography paper.

EXAMPLE 2

Synthesis of an Ethylenediaminetrispropiohydroxamnic Acid Chelator (EDTHA) N,N,N'-tris[2-(tert-butoxycarbonyl)ethyl]-2-(2-aminoethylamino)ethanol (1)

A solution of 2-(2-aminoethylamino)ethanol (5 mL; 5.15 g; 49.4 mmole) in 35 mL (30.905 g; 241.1 mmole) of tert-butyl acrylate was heated at reflux for 16.4 hours. The excess reagent was removed under reduced pressure and the resulting oil was purified by flash chromatography using a mixture of dichloromethane, methanol, and ammonium hydroxide (94:5:1) to elute the desired material. Fractions were collected and analyzed to determine which of these contain the product. Solvents were eliminated under vacuum to give 19.13 g (79.2%) of N,N,N'-tris[2-(tert-butoxycarbonylethyl)]-2-(2-aminoethylamino)ethanol (1) as a pale yellow oil.

$^1$H NMR (in $CDCl_3$; 400 MHz): 3.52 (t, 2H, J=5.0 Hz, HOC$\underline{H}_2$CH$_2$N(R)—), 2.80 (t, 2H, J=7.0 Hz, —(R)NCH$_2$C$\underline{H}_2$CO$_2$C(CH$_3$)$_3$), 2.73 (t, 4H, J=7.5 Hz, —(R)NCH$_2$C$\underline{H}_2$CO$_2$C(CH$_3$)$_3$), 2.58 (t, 2H, J=5.0 Hz, HOCH$_2$C$\underline{H}_2$N(R)—), 2.55 (m, 2H, —(R)NC$\underline{H}_2$CH$_2$N(R)—), 2.48 (m, 2H, —(R)NCH$_2$C$\underline{H}_2$N(R)—), 2.55 (t, 6H, J=7.4 Hz, —(R)NC$\underline{H}_2$CH$_2$CO$_2$C(CH$_3$)$_3$), 1.43 (s, 9H, —CO$_2$C(C$\underline{H}_3$)$_3$), and 1.42 ppm (s, 18H), —CO$_2$C(C$\underline{H}_3$)$_3$). $^{13}$C NMR (in $CDCl_3$; 75 MHz): 172.0 (2C, —$\underline{C}$O$_2$C (CH$_3$)$_3$), 171.8 (1C, —CO$_2$C(CH$_3$)$_3$), 80.5 (2C, —CO$_2$$\underline{C}$(CH$_3$)$_3$), 80.3 (1C, —CO$_2$$\underline{C}$(CH$_3$)$_3$), 59.6 (1C, HOC$\underline{H}_2$CH$_2$N(R)—), 55.8 (1C, HOCH$_2$$\underline{C}$H$_2$N(R)—), 52.4 (1C, —N(R)$\underline{C}$H$_2$CH$_2$N(R)—), 51.9 (1C, —N(R)CH$_2$$\underline{C}$H$_2$N(R)—), 50.5 (1C, —N(R)$\underline{C}$H$_2$CH$_2$CO$_2$tBu), 49.3 (2C, —N(R)$\underline{C}$H$_2$CH$_2$CO$_2$tBu), 33.8 (1C, —N(R)CH$_2$$\underline{C}$H$_2$CO$_2$tBu), 33.2 (2C, —N(R)CH$\underline{C}$CH$_2$CO$_2$tBu), and 28.0 ppm (9C, —CO$_2$C(C$\underline{H}_3$)$_3$). MS (m/z, EI): 490 ($M^+$+1), 489 ($M^+$), 415 ($M^+$-[(CH$_3$)$_3$COH]), 373 ($M^+$-[(CH$_3$)$_3$O$_2$CCH$_3$]), 299, 287, 286 (100%), 230, 202, 174, 146, and 57 (($CH_3)_3C^+$). IR (film, NaCl disks): 3490 (0-H), 2975 (C—H), 2930 (C—H), 2820, 1725 (C=0), 1455, 1390, 1365, 1255, 1155, 1030, 980, 950, 845, 750, and 730 cm$^{-1}$.

N-[2-(2',4',6'-trimethylphenylcarbonyloxy)ethyl]N,N,N'-tris[2-(tertbutoxycarbo-nyl)ethyl]-1,2-ethylenediamine (2)

Pyridine (1.8 mL; 1.76 g; 22.3 mmole) was added to a solution of N,N,N'-tris[2-(tert-butoxycarbonylethyl)]-2-(2-aminoethylamino)ethanol (1) (2.1452 g; 4.4 mmole) solubilized in dry methylene chloride (20 mL). This mixture was cooled to 0° C. with an ice bath and a solution of 2,4,6-trimethylbenzoyl chloride (2.4338 g; 13.3 mmole) in dry dichloromethane was slowly added to it. The reaction mixture was stirred overnight while leaving its temperature raising gradually to 20° C. Water (125 mL) was added to the mixture and the two layers were separated. The organic phase was washed another time with water (125 mL) then with a saturated sodium bicarbonate solution (2×125 mL) and brine (150 mL). The organic solution was dried over magnesium sulfate, filtered, and the solvent was removed under reduced pressure. The obtained residue was purified by flash chromatography on silica gel using a mixture of dichloromethane, ethyl acetate, and N,N-diisopropylethylamine (79.9/20/0.1) to elute the desired product. 2.29 g (82.2%) of N-[2-(2',4',6'-trimethylphenylcarbonyloxy)ethyl],N,N,N'-tris[2-(tert-butoxycarbonyl)ethyl]-1,2-ethylenediamine (2) was recovered from the purification.

$^1$H NMR (in CDCl$_3$; 300 MHz): 7.26 (s, 2H, (CH$_3$)$_3$C$_6$H$_2$CO$_2$—), 4.34 (t, 2H, J=6.5 Hz, (CH$_3$)$_3$C$_6$H$_2$CO$_2$CH$_2$CH$_2$N(R)—), 2.83 (t, 2H, J=6.8 Hz, —(R)NCH$_2$CH$_2$CO$_2$C(CH$_3$)$_3$), 2.81 (t, 2H, J=6.4 Hz, (CH$_3$)$_3$C$_6$H$_2$CO$_2$CH$_2$CH$_2$N(R)—), 2.71 (t, 4H, J=7.3 Hz, —(R)NCH$_2$—CH$_2$CO$_2$C(CH$_3$)$_3$), 2.60 (m, 2H, —(R)NCH$_2$CH$_2$CN(R)—), 2.51 (m, 2H, —(R)NCH$_2$—CH$_2$CN(R)—), 2.36 (t, 2H, J=7.7 Hz, —(R)NCH$_2$CH$_2$CO$_2$C(CH$_3$)$_3$), 2.33 (t, 2H, J=7.4 Hz, —(R)NCH$_2$CH$_2$CO$_2$C(CH$_3$)$_3$), 2.29 (s, 6H, CH$_3$—C$_{2'arom}$ and CH$_3$—C$_{6'arom}$), 2.27 (s, 3H, CH$_3$—C$_{4'arom}$), 1.44 (s, 18H, —CO$_2$C(CH$_3$)$_3$), and 1.43 ppm (s, 9H, —CO$_2$C(CH$_3$)$_3$).

N-[2-(2',4',6'-trimethylphenylcarbonyloxy)ethyl],N,N,N'-tris[2-hydroxycarbonyl-ethyl]-1,2-ethylenediamine (3)

A solution of tributyl ester (2) (142.2 mg; 224 μmole) in 6 mL of dry dichloromethane was poured into a 25 mL round bottom flask. This solution was stirred at room temperature and trifluoroacetic acid (6 mL; 9.21 g; 80.8 mmole) was added to it. After 3.3 hours of reaction, the mixture was concentrated under reduced pressure. The residue was triturated twice with benzene and the solvent was removed under vacuum. 0.1N Hydrochloric acid (15 mL) was added to the residue and the resulting mixture was stirred for 15 minutes before removing the volatile substances. This process was repeated another time and the residual solid was dried by trituration with benzene (2×15 mL). The solid was then filtered and dried under vacuum.

N-[2-(2',4',6'-trimethylphenylcarbonyloxy)ethyl],N,N,N'-tris[2(benzyloxyamnino-carbonylethyl)]-1,2-ethylenediamine (4)

Trifluoroacetic acid (7.5 mL; 11.5125 g; 101 mmole) and trisisopropylsilane (320 μL; 247.4 mg; 1.6 mmole) were added to a solution of N$^1$-[2-(2',4',6'-trimethyl-phenylcarbonyloxy)ethyl],N$^1$,N$^2$,N$^2$-tris[2-(tert-butoxycarbonyl)ethyl]-1,2-ethylenediami-ne (2) (392.8 mg; 0.6 mmole) in dry dichloromethane (7.5 mL). The reaction mixture was stirred at room temperature for 3 hours and the volatile substances were removed under reduced pressure. The residue was treated with 30 mL of 0.1N hydrochloric acid for several minutes, then the mixture was concentrated under vacuum. This process was repeated another time and the final residue was dried overnight in vacuo. The desired material was used without further purification to achieve the next step.

A suspension of the crude N-[2-(2',4',6'-trimethylphenylcarbonyloxy)ethyl], N,N,N'-tris[2-(hydroxycarbonylethyl)]-1,2-ethylenediamine dihydrochloride (3) (0.6 mmole) and O-benzyl hydroxylamine hydrochloride (743.3 mg; 4.7 mmole) in acetonitrile (20 mL) was stirred at room temperature. 1-(3-dimethylaminopropyl)-3-ethylcarbodiimide hydrochloride (1.468 g; 7.0 mmole) and 4-(N,N-dimethylamino)pyridine (58.2 mg; 0.48 mmole) were added while stirring vigorously the mixture. Another quantity of 4-(N,N-dimethylamino)pyridine (55 mg; 0.45 mmole) was added after two hours of reaction. The reaction continued for an extra 120 hours followed by the addition of water (125 mL) and ethyl acetate (100 mL). The two layers were separated and the aqueous one was extracted twice with 100 mL of ethyl acetate. The organic layers were combined, washed successively with 0.2M citric acid pH 5.25 (3×125 mL) and brine (3×100 mL), dried on magnesium sulfate, filtered, and finally evaporated to dryness under reduced pressure. The resulting yellow oil (366 mg) was purified by flash chromatography on silica gel using a mixture of dichloromethane and methanol (92:8) as eluent. The purification gave 310 mg (64.1%; two steps) of the desired compound (4) as a colorless oil.

$^1$H NMR (in CD$_3$OD; 400 MHz): 7.34 (m, 15H, —C(O)NHOCH$_2$C$_6$H$_5$), 6.83 (s, 2H, (CH$_3$)$_3$C$_6$H$_2$CO$_2$—), 4.82 (s, 4H, —C(O)NHOCH$_2$C$_6$H$_5$), 4.74 (s, 2H, —C(O)NHOCH$_2$C$_6$H$_5$), 4.34 (t, 2H, J=6.0 Hz, (CH$_3$)$_3$C$_6$H$_2$CO$_2$CH$_2$CH$_2$N(R)—), 2.80 (t, 4H, J=5.9 Hz, —(R)NCH$_2$CH$_2$CONHOBn), 2.66 (t, 4H, J=6.4 Hz, —(R)NCH$_2$CH$_2$CONHOBn), 2.55 (m, 2H, —(R)NCH$_2$CH$_2$CN(R)—), 2.47 (m, 2H, —(R)NCH$_2$CH$_2$N(R)—), 2.23 (s, 6H, CH$_3$—C$_{2'arom}$ and CH$_3$—C$_{6'arom}$), 2.22 (s, 3H, CH$_3$—C$_{4'arom}$), 2.21 (m, 2H, —(R)NCH$_2$CH$_2$CONHOBn), and 2.16 ppm (t, 4H, J=6.5 Hz, —(R)NCH$_2$CH$_2$CONHOBn). $^1$H NMR (in CDCl$_3$; 400 MHz): 9.83 (bs, 3H, —C(O)NHOCH$_2$C$_6$H$_5$), 7.29 (m, 15H, —C(O)NHOCH$_2$C$_6$H$_5$), 6.83 (s, 2H, (CH$_3$)$_3$C$_6$H$_2$CO$_2$—), 4.77 (s, 4H, —C(O)NHOCH$_2$C$_6$H$_5$), 4.74 (s, 2H, —C(O)NHOCH$_2$C$_6$H$_5$), 4.15 (t, 2H, J=5.3 Hz, (CH$_3$)$_3$C$_6$H$_2$CO$_2$CH$_2$CH$_2$N(R)—), 2.69 (t, 2H, J=6.5 Hz, —(R)NCH$_2$CH$_2$CONHOBn), 2.64 (t, 2H, J=6.0 Hz, —(R)NCH$_2$CH$_2$CONHOBn), 2.55 (m, 4H, —(R)NCH$_2$CH$_2$—CONHOBn and (CH$_3$)$_3$C$_6$H$_2$CO$_2$CH$_2$CH$_2$N(R)—), 2.36 (m, 2H, —(R)NCH$_2$CH$_2$CN(R)—), 2.30 (m, 2H, —(R)NCH$_2$—CH$_2$CN(R)—), 2.26 (s, 3H, CH$_3$—C$_{4'arom}$), 2.24 (s, 6H, CH$_3$—C$_{2'arom}$+CH$_3$—C$_{6'arom}$), 2.18 (t, 2H, J=6.6 Hz, —(R)NCH$_2$CH$_2$CONHOBn), 2.07 ppm (m, 4H, —(R)NCH$_2$CH$_2$CONHOBn). MS (m/z, ES): 805.5 (M$^+$+Na), 804.4 (M$^+$+Na-1H, 100%), 783.5 (M$^+$+2), 782.5 (M$^+$+1), 606.5, and 605.5. FT-IR (CDCl$_3$, NaCl cells): 3240 (bs, N—H), 3040 (C—H$_{arom}$), 2950 (C—H), 2820 (C—H$_{aliph}$), 1715 (C=O), 1705 (C=O), 1680 (C=O), 1495, 1460, 1365, 1265, 1170, and 1085 cm$^{-1}$.

N,N,N'-tris[2-(benzyloxyaminocarbonylethyl)]-2-(2-aminoethylamino)ethanol (5)

2-(2-aminoethylamino)ethanol (51.5 mg; 0.5 mmole) was added to a solution of N-benzyloxy acrylamide (30) (279.4 mg; 1.6 mmole) solubilized in tetrahydrofuran (10 mL). The resulting solution was heated at reflux for 24 hours and stirred at room temperature for 5 additional days. The solvent was then removed under to give 373 mg of a yellow oil. The residue was purified by flash chromatography and a mixture of dichloromethane and methanol (90:10) was used to elute the product. 255.5 mg (81.4%) of the desired substance (5) was isolated from the purification as an almost colorless viscous oil.

$^1$H NMR (in CDCl$_3$; 300 MHz): 7.32 (m, 15H, —C(O)NHOCH$_2$C$_6$H$_5$), 4.83 (s, 2H, —C(O)NHOCH$_2$C$_6$H$_5$), 4.79 (s, 4H, —C(O)NHOCH$_2$C$_6$H$_5$), 3.43 (m, 2H, HOCH$_2$CH$_2$N(R)—), 2.63 (t, J=6.6 Hz, 2H), 2.57 (t, 4H, J=5.3 Hz), 2.42 (m, 2H, HOCH$_2$CH$_2$N(R)—), 2.34 (m, 2H), 2.31 (m, 2H), 2.20 (t, 2H, J=6.5 Hz), 2.15 (t, 4H, J=5.1 Hz), 1.58 ppm (bs, 3H, —C(O)NHOCH$_2$C$_6$H$_5$). $^1$H NMR (in Acetone-D$_6$; 300 MHz): 7.36 (m, 15H, H$_{arom}$), 4.87 (s, 4H, —CONHCH$_2$C$_6$H$_5$), 4.85 (s, 2H, —CONHCH$_2$C$_6$H$_5$), 3.53 (t, 2H, J=5.4 Hz, HOCH$_2$CH$_2$N(R)—), 2.80 (m, 9H), 2.67 (t, 2H, J=6.0 Hz), 2.50 (m, 7H), 2.22 ppm (t, 6H, J=5.7 Hz). $^{13}$C NMR (in CDCl$_3$; 75 MHz): 170.9 (2C, —CH$_2$CONHOCH$_2$C$_6$H$_5$), 170.6 (1C, —CH$_2$CONHOCH$_2$C$_6$H$_5$), 135.4 (3C, —$C_{1arom}$), 128.8 (6C, H—$C_{2arom}$ and H—$C_{6arom}$), 128.2 (9C, H—$C_{3arom}$, H—$C_{4arom}$, and H—$C_{5arom}$), 77.7 (3C, —$CH_2CONHO\underline{C}H_2C_6H_5$), 59.0 (1C, HO$\underline{C}H_2CH_2NR$—), 56.1 (1C, HOC$H_2\underline{C}H_2NR$—), 52.6 (1C, —N(R)$\underline{C}H_2CH_2N(R)$—), 52.1 (1C, —N(R)$CH_2\underline{C}H_2N(R)$—), 49.9 (2C, —N(R)$\underline{C}H_2CH_2N(R)$—), 49.7 (1C, —N(R)$CH_2\underline{C}H_2$—CONHOBn), 31.3 (2C, —N(R)$\underline{C}H_2CH_2$CONHOBn), and 31.1 ppm (1C, —N(R)$CH_2\underline{C}H_2$CONHOBn). IR (film, NaCl disks): 3190 (bs, H—O and N—H), 3015 (C—$H_{arom}$), 2980 (C—$H_{aliph}$), 2810, 1650 (C=O), 1495, 1450, 1365, 1210, 1060, 1020, 905, 745, and 695 cm$^{-1}$.

N-[2-(benzoyloxy)ethyl],N,N,N'-tris[2-(tert-butoxycarbonylethyl)]-1,2-ethylenediamine (6)

Pyridine (420 μL; 410.8 mg; 5.2 mmole) was added to a cooled solution of tert-butyl hydroxytrispropionate (1) (826.9 mg; 1.7 mmole) dissolved in dichloromethane (20 mL). The mixture was stirred at 0° C. for about 10 minutes followed by the slow addition of benzoyl chloride (290.6 mg; 2.1 mmole). The temperature of the reaction mixture was kept at 0° C. for one hour then it was left alone to warm up until it reaches room temperature. Water (~100 mL) was added to the reaction after 67.3 hours. The organic layer was separated and washed two times with a saturated sodium bicarbonate solution (100 mL each) and brine (100 mL). The organic layer was then dried with magnesium sulfate, filtered, and the solvent was removed under vacuum. The residue was purified by flash chromatography (dichloromethane/ethyl acetate/N,N-diisopropyl-ethylamine; 79.9: 20:0.1). N-[2-(benzoyloxy)ethyl],N,N,N'-tris[2-(tertbutoxycarbonyl-ethyl)]-1,2-ethylenediamine (6) (811.7 mg; 80.9%) was recovered after the purification.

$^1$H NMR (in CDCl$_3$, 300 Mz): 8.04 (dd, 2H, J=1.1 and 8.4 Hz, $\underline{H}$—$C_{2'arom}$ and $\underline{H}$—$C_{6'arom}$), 7.55 (t, 1H, J=7.5 Hz, $\underline{H}$—$C_{4'arom}$), 7.43 (t, 2H, J=7.5 Hz, $\underline{H}$—$C_{3'arom}$ and $\underline{H}$—$C_{5'arom}$), 4.36 (t, 2H, J=6.2 Hz, $C_6H_5CO_2C\underline{H}_2CH_2N(R)$—), 2.86 (t, 4H, J=6.4 Hz, $C_6H_5CO_2CH_2C\underline{H}_2N(R)$— and —(R)NCH$_2$C$\underline{H}_2CO_2C(CH_3)_3$), 2.73 (t, 4H, J=7.3 Hz, —(R)NCH$_2$C$\underline{H}_2CO_2C(CH_3)_3$), 2.62 (m, 2H, —(R)NC$\underline{H}_2CH_2N(R)$—), 2.53 (m, 2H, —(R)NC$\underline{H}_2CH_2N(R)$—), 2.38 (t, 2H, J=7.4 Hz, —(R)NC$\underline{H}_2CH_2CO_2C(CH_3)_3$), 2.34 (t, 4H, J=7.3 Hz, —(R)NC$\underline{H}_2CH_2CO_2C(CH3)3$), and 1.43 ppm (s, 27H, —$CO_2C(C\underline{H}_3)_3$). MS (m/z, ES): 593 (M$^+$), 519 (M$^+$-[(CH$_3$)$_3$COH]), 477 (M$^+$-[(CH$_3$)$_3$CO$_2$CCH$_3$]), 306, 299, 287, 286 (100%), 250, 230, 174, 149 (C$_6$H$_5$CO$_2$CH$_2$CH$_2^+$), and 57 ((CH$_3$)$_3$C$^+$). IR (film, NaCl disks): 2970 (C—$H_{arom}$), 2930 (C—$H_{aliph}$), 2815 (C—$H_{aliph}$), 1725 (C=O), 1715 (C=O), 1450, 1390, 1365, 1310, 1270, 1150, 1110, 1065, 1025, 845, 750, and 705 cm$^{-1}$.

N-[2-phthalimidoethyl],N,N,N'-tris[2-tert-butoxycarbonylethyl]-1,2-ethylenediamine (7)

Diethyl azodicarboxylate (500 μL; 553 mg; 3.2 mmole) was added to a cooled solution of N,N,N'-tris[2-(tert-butoxycarbonylethyl)]-2-(2-aminoethylamino)ethanol (1) (621.2 mg; 1.3 mmole), phthalimide (468.1 mg; 3.2 mmole), and triphenylphosphine (833.7 mg; 3.2 mmole) dissolved in dry tetrahydrofuran (18 mL). The reaction mixture was kept at 0° C. for about an hour and stirred for another 21.75 hours while the temperature was left to warm up slowly. Water (10 mL) was added and the mixture was concentrated under reduced pressure to give 2.58 g of a yellow solid. This residue was dissolved with a mixture of water and diethyl ether. The organic layer was washed two more times with water, dried with magnesium sulfate, and filtered. The solvent was removed under vacuum. The crude material was purified by flash chromatography on silica gel using a mixture of dichloromethane and ethyl acetate (70:30) to elute the compound. The purification produce 385 mg (49%) N-[2-phthalimidoethyl],N,N,N'-tris[2-tert-butoxycarbonylethyl]-1, 2-ethylenediamine (7) as a yellow oil.

$^1$H NMR (in CDCl$_3$, 300 MHz): 7.84 (dd, J=3.1 and 5.4 Hz, $\underline{H}C_{3'arom}$ and $\underline{H}$—$C_{6'arom}$), 7.70 (dd, 2H, J=3.0 and 5.4 Hz, $\underline{H}$—$C_{4'arom}$ and $\underline{H}$—$C_{5'arom}$), 3.75 (t, 2H, J=6.7 Hz, PhthHNC$\underline{H}_2CH_2N(R)$—), 2.79 (t, 2H, J=7.3 Hz, —(R)NCH$_2$C$\underline{H}_2CO_2C(CH_3)_3$), 2.71 (t, 6H, J=7.4 Hz, PhthHNCH$_2$C$\underline{H}_2N(R)$— and —(R)NCH$_2$C$\underline{H}_2CO_2C(CH_3)_3$), 2.56 (m, 2H, —(R)NC$\underline{H}_2CH_2N(R)$—), 2.45 (m, 2H, —(R)NCH$_2$C$\underline{H}_2N(R)$—), 2.33 (t, 4H, J=7.4 Hz, —(R)NC$\underline{H}_2CH_2CO_2C(CH_3)_3$), 2.30 (t, 2H, J=7.2 Hz, —(R)NC$\underline{H}_2CH_2$—$CO_2C(CH_3)_3$), 1.44 (s, 18H, —$CO_2C(CH_3)_3$), and 1.39 ppm (s, 9H, —$CO_2C(C\underline{H}_3)_3$).

N,N,N'-tris[2-benzyloxycarbonylethyl]-2-(2-aminoethylamino)ethanol (8)

A solution of 2-(2-aminoethylamino)ethanol (4.6648 g; 44.8 mmole) dissolved in 35 mL of benzyl acrylate was heated at reflux for 24 hours. The excess reagent was removed under reduced pressure and the resulting oil was purified by flash chromatography using a mixture of dichloromethane and ethyl acetate (60:40) to elute the desired material. Fractions were collected and analyzed to determine which of these contain the product. Solvents were eliminated under vacuum to give 5.8 g (21.9%) of N,N,N'-tris[2-(benzyloxycarbonylethyl]-2-(2aminoethylamino)ethanol (8).

$^1$H NMR (in CDCl$_3$; 300 MHz): 7.37 (sl, 15H, —$CO_2CH_2C_6\underline{H}_5$), 5.10 (s, 2H, —$CO_2C\underline{H}_2C_6H_5$), 5.09 (s, 4H, —$CO_2C\underline{H}_2C_6H_5$), 3.49 (t, 2H, J=5.0 Hz, HOC$\underline{H}_2CH_2N(R)$—), 2.82 (t, 2H, J=6.9 Hz, —N(R)C$\underline{H}_2$—CH$_2$CO$_2$Bn), 2.76 (t, 6H, J=7.2 Hz, HOCH$_2$C$\underline{H}_2N(R)$— and —N(R)CH$_2$C$\underline{H}_2CO_2Bn$), 2.49 (m, 4H, —N(R)C$\underline{H}_2$C$\underline{H}_2N(R)$—), and 2.47 ppm (t, 6H, J=6.9 Hz, —N(R)C$\underline{H}_2CH_2CO_2Bn$). IR (film, NaCl disks): 3460 (bs, H—O), 3060 (C—$H_{arom}$), 3015 (C—$H_{arom}$), 2950 (C—$H_{aliph}$), 2810 (C—$H_{aliph}$), 1735 (C=O, esters), 1495, 1455, 1370, 1255, 1170, 1025, 750, and 695 cm$^{-1}$.

N-[2-(tert-butyldiphenylsilyloxyethyl],N,N,N'-tris[2-benzyloxycarbonyl-ethyl]-1,2-ethylenediamine (9)

N,N,N'-tris[2-(benzyloxycarbonylethyl]-2-(2-aminoethylamino)ethanol (8) (1.0734 g; 1.8 mmole) was placed in a 100 mL round bottom flask and dry dichloromethane (30 mL) was added to dissolve the product. Triethylamine (280 μL; 203 mg; 2.0 mmole) and 4-(N,N-dimethylamino)pyridine (10.3 mg; 0.1 mmole) were added to the solution and stirred for 15 minutes before adding 520 μL (549.6 mg; 2.0 mmole) of tert-butylchlorodiphenylsilane. The reaction mixture was stirred at room temperature for an additional 20.5 hours and then washed two times with water (50 mL each washes) and 10% ammonium chloride (50 mL each washes). The organic layer was dried with sodium sulfate, filtered, and concentrated under vacuum. Purification by flash chromatography (dichloromethane:ethyl acetate; 85:15) gave 0.85 g (56.4%) of the desired compound (9) as an oil.

$^1$H NMR (in CDCl$_3$; 300 MHz): 7.65 (dd, 4H, J=2.0 and 7.4 Hz, $\underline{H}$—$C_{2'arom}$ and $\underline{H}$—$C_{6'arom}$-phenyl from silyl ether), 7.33 (m, 21H, H—C$_{arom}$-benzyl ester and phenyl from silyl ether), 5.07 (s, 4H, —CO$_2$CH$_2$C$_6$H$_5$), 5.05 (s, 2H, —CO$_2$C H$_2$C$_6$H$_5$), 3.63 (t, 2H, J=6.5 Hz, TBDPSOCH$_2$CH$_2$N(R)—), 2.77 (t, 2H, J=7.3 Hz, —N(R)CH$_2$CH$_2$CO$_2$Bn), 2.71 (t, 4H, J=7.2 Hz, —N(R)CH$_2$CH$_2$CO$_2$Bn), 2.57 (t, 2H, J=6.5 Hz, TBDPSOCH$_2$CH$_2$N(R)—), 2.4 (m, 10H, —N(R)CH$_2$C H$_2$N(R)— and —N(R)CH$_2$CH$_2$CO$_2$Bn), and 1.02 ppm (s, 9H, —OSi(Ph)$_2$C(CH$_3$)$_3$). IR (film, NaCl disks): 3060 (C—H$_{arom}$), 3015 (C—H$_{arom}$), 2950 (C—H$_{aliph}$), 2930 (C—H$_{aliph}$), 2850 (C—H$_{aliph}$), 1735 (C=0, ester), 1450, 1425, 1160, 1105, 730, and 695 cm$^{-1}$.

EXAMPLE 3

Synthesis of a Trisaminopropane Tetrapropiohydroxamic Acid Chelator (TPTHA) N$^1$,N$^3$-bis(tert-butoxycarbonyl)-1,3-diamino-2-propanol (10)

A solution of 2-hydroxy-1,3-diaminopropane (11.88 g; 0.132 mole) in 100 mL of water was poured into a 500 mL round bottom flask and cooled to 0 CC with an ice bath. A mixture of tert-butyl dicarbonate (72.02 g; 0.330 mole; 2.5 eq) in 1,4-dioxane (150 mL) was then added to the cooled solution. To the vigorously stirred reaction mixture was added sodium carbonate (29.57 g; 0.279 mole; 2.1 eq) in small portions. After 50 hours of reaction the solvent were eliminated under reduced pressure to give an off-white solid (37.72 g). Recrystallisation of the residue with a mixture of diethyl ether and hexane produced the desired bisprotected 1,3-diamino-2-propanol (10) as a white amorphous solid in excellent yield (35.00 g; 91.4%).

$^1$H NMR (in CDCl$_3$+TMS; 300 MHz): 5.12 (bs, 2H, Boc HNCH$_2$CH(OH)CH$_2$NHBoc), 3.75 (tt, J=4.8 and 5.5 Hz, 1H, BocHNCH$_2$CH(OH)CH$_2$NHBoc), 3.28 (dd, J=4.1 and 14.2 Hz, 2H, BocHNCH$_\alpha$CH(OH)CH$_\alpha$NHBoc), 3.16 (dd, J=5.4 and 14.3 Hz, 2H, BocHNCH$_\beta$CH(OH)CH$_\beta$NHBoc), 2.53 (bs, 1H, BocHNCH$_2$CH(OH)CH$_2$NHBoc), and 1.45 ppm (s, 18H, —NHCO$_2$C(CH$_3$)$_3$). $^{13}$C NMR (in CDCl$_3$; 100 MHz): 157.66 (2C, —HNCO$_2$C(CH$_3$)$_3$), 80.26 (2C, —HNCO$_2$C(CH$_3$)$_3$), 71.56 (1C, BocHNCH$_2$CH(OH)—CH$_2$NHBoc), 44.00 (2C, BocHNCH$_2$CH(OH) CH$_2$NHBoc), 28.79 ppm (6C, —HNCO$_2$C(CH$_3$)$_3$). MS (m/z, EI): 292, 291 (M$^+$+1), 236, 235, 180, 179, 178, 161, 160, 159, 135, 117, 116, 105, 104 (100%), 87, 76, and 75. FT-IR (CDCl$_3$, NaCl cells): 3456 (—OH), 2981(C—H$_{aliph\&arom}$), 2934 (C—H$_{aliph\&arom}$), 1701 (C=0), 1508, 1368, 1250, and 1167 cm$^{-1}$.

N$^1$,N$^3$-bis(tert-butoxycarbonyl)-2-methanesulfonyloxy-1,3-diaminopropane (11)

A mixture of the diprotected 1,3-diamino-2-propanol (10) (15.0 g; 51.7 mmole) and triethylamine (11.6 mL; 8.42 g; 83.2 mmole) in 80 mL of dry dichloromethane was cooled to 0° C. with an ice bath. Methanesulfonyl chloride (5 mL; 7.4 g; 64.6 mmole) was then slowly added. The reaction mixture was kept at 0° C. for about two hours and then stirred overnight while the reaction was allowed to warm to room temperature. Water (40 mL) was added and the two layers were separated. The aqueous layer was extracted with dichloromethane, and the combined extracts were dried with magnesium sulfate and filtered. The filtrate was concentrated by rotatory evaporation to give a yellow solid. The residue was triturated with a hot mixture of hexane and ether, filtered and dried under reduced pressure. This purification gave 16.08 g (84.5%) of the di-(tert-butoxycarbonylamino)mesylate (11) as a pale beige solid.

$^1$H NMR (in CDCl$_3$; 300 MHz): 5.16 (bs, 2H, Boc HNCH$_2$CH(OMs)CH$_2$NHBoc), 4.67 (qn, J=4.8 Hz, 1H, BocHNCH$_2$CH(OMs)CH$_2$NHBoc), 3.50 (ddd, 2H, J=4.5, 7.3, and 14.7 Hz, BocHNCH$_\alpha$CH(OMs)CH$_\alpha$NHBoc), 3.31 (dt, J=5.8 and 14.7 Hz, 2H, BocHNCH$_\beta$CH(OMs)C H$_\beta$NHBoc), 3.34 (s, 3H, —CH(OSO$_2$CH$_3$)—) and 1.45 ppm (s, 18H, —NHCO$_2$C(CH$_3$)$_3$). $^{13}$C NMR (in CDCl$_3$; 100 MHz): 156.74 (2C, —HNCO$_2$C(CH$_3$)$_3$), 80.47 (2C, —NHCO$_2$C(CH$_3$)$_3$), 79.46 (1C, BocHNCH$_2$ CH(OMs)CH$_2$NHBoc), 41.21 (2C, BocHNCH$_2$CH(OMs) CH$_2$NHBoc), 38.58 (1C, —OSO$_2$CH$_3$), and 28.73 ppm (6C, —HNCO$_2$C(CH$_3$)$_3$). MS (m/z, EI): 368 (w, M$^+$), 282, 239, 215, 195, 177, 159 (100%), 143, 116, 115, 104, and 99. FT-IR (CDCl$_3$, NaCl cells): 3455 (—OH), 2982 (C—H$_{aliph\&arom}$), 1708 (C=0), 1509, 1368, 1247, and 1176 cm$^-$.

N$^1$,N$^3$-bis-(tert-butoxycarbonyl)-2-azido-1,3-diaminopropane (12)

To a solution of the di-(tert-butoxycarbonylamino)mesylate (11) (4.0334 g; 10.9 mmole) in N,N-dimethylformamide (40 mL) was added sodium azide (2.857 g; 43.9 mmole). The reaction mixture was stirred at 70° C. for 24 hours. The solvent was removed in vacuo and the residue was redissolved in ethyl acetate (125 mL) and water (125 mL). The two layers were separated and the aqueous layer was extracted two more times with ethyl acetate. The combined organic layers were dried over magnesium sulfate, filtered, and evaporated in vacuo. The almost colorless oil was purified by flash column chromatography using a mixture of hexane-ethyl acetate (75:25). The purification produced 3.24 g (93.9%) of N$^1$,N$^3$-bis-(tert-butoxycarbonyl)-2-azido-1,3-diaminopropane (12) as a white solid.

$^1$H NMR (in CDCl$_3$; 500 MHz): 5.08 (Boc HNCH$_2$CH(N$_3$)CH$_2$NHBoc), 3.65 (t$_{app}$, 1H, J=5.2 Hz, BocHNCH$_2$CH(N$_3$)CH$_2$NHBoc), 3.38 (m, 2H, BocHNC H$_\alpha$CH(N$_3$)—CH$_\alpha$NHBoc), 3.14 (m, 2H, BocHNC H$_\beta$CH(N$_3$)CH$_\beta$NHBoc), and 1.45 ppm (—NHCO$_2$C(C H$_3$)$_3$). $^{13}$C NMR (in CDCl$_3$; 100 MHz): 156.62 (2, —HN CO$_2$C(CH$_3$)$_3$), 80.33 (2C, —HNCOC(CH$_3$)$_3$), 61.34 (1C, BocHNCH$_2$CH(N$_3$)CH$_2$NHBoc), 41.21 (2C, BocHN CH$_2$CH(N$_3$)CH$_2$NHBoc), and 28.76 (6C, —NHCO$_2$C( CH$_3$)$_3$). MS (m/z, EI): 317, 316 (M$^+$+1), 261, 260, 216, 215 (M+-C$_5$H$_8$O$_2$), 205, 204 (100; C$_5$H$_9$O$_2$), 187, 186, 175, 161, 160, 159, 149, 148, 143, 142, 130, 129, 116, 115, 103, 102, 101, 97, 86, 85, 84, 76, 75, 74, and 71.

N$^1$,N$^3$-bis-(tert-butoxycarbonyl)-1,2,3-triaminopropane (13)

A solution of N$^1$,N$^3$-bis-(tert-butoxycarbonyl)-2-azido-1, 3-diaminopropane (12) (1.1502 g; 3.65 mmole) in methanol (35 mL) was poured into a Parr hydrogenation bottle. A palladium catalyst (10%/C; 174 mg) was added to the solution and the resulting mixture was placed in a Parr hydrogenation apparatus. The mixture was degassed under reduced pressure followed by the introduction of a hydrogen atmosphere (50 psi). The reaction was vigorously shaken for 17.5 hours and the hydrogen was removed in vacuo. The catalyst was then filtered off over celite and the filtrate was concentrated by rotatory evaporation to give a white solid (1.019 g; 96.6%).

$^1$H NMR (in CDCl$_3$; 600 MHz): 5.20 (bs, 2H, Boc HNCH$_2$CH(NH$_2$)CH$_2$NHBoc), 3.14 (m, 2H, BocHNC H$_\alpha$CH(NH$_2$)CH$_\alpha$NHBoc), 3.08 (m, 2H, BocHNC H$_\beta$CH(NH$_2$)—CH$_\beta$NHBoc), 2.93 (qn, 1H, J=5.5 Hz, BocHNCH$_2$CH(NH$_2$)CH$_2$NHBoc), and 1.44 ppm (s, 18H, —NHCO$_2$C(CH$_3$)$_3$). $^{13}$C NMR (CDCl$_3$; 100 MHz): 157.08 (2C, —HNCO$_2$C(CH$_3$)$_3$), 79.87 (2C, —HNCO$_2$C(CH$_3$)$_3$), 51.79 (1C, BocHNCH$_2$CH(NH$_2$)CH$_2$NHBoc), 44.11 (2C, BocHNCH$_2$CH(NH$_2$)CH$_2$NHBoc), and 28.81 ppm (6C, —NHCO$_2$C(CH$_3$)$_3$). MS (m/z, EI): 290 (w, M$^+$+1), 160, 103 (100%), 85, 59, 57 ((CH$_3$)$_3$C$^+$), 43, and 41.

Benzyl N-[2-[1,3-bis(tert-butoxycarbonylamino)]propyl]succinamate (14)

In a 25 mL flame-dried three-necked, round-bottom flask equipped with an addition funnel, a septum, and a stopper are placed mono-benzyl succinate (19) (433.5 mg; 2.1 mmole), 1-hydroxybenzotriazole hydrate (282.4 mg; 2.09 mmole), N,N-diisopropylethylamine (5461 µL; 405 mg; 3.1 mmole), and dry ethyl acetate (10 mL). The resulting solution was cooled to 0° C. with an ice bath followed by addition of 2.09 mL (2.09 mmole) of a 1M N,N'-dicyclohexylcarbodiimide in dichloromethane solution. The mixture was stirred for ten minutes under an atmosphere of argon before adding slowly a solution of N$^1$,N$^3$-bis-(tert-butoxycarbonyl)-1,2,3-triaminopropane (13) (603.7 mg; 2.08 mmole) dissolved in 10 mL of dry ethyl acetate. After 17.7 hours at room temperature, the reaction mixture was filtered on celite. The filtrate was washed with a saturated solution of sodium bicarbonate (3×120 mL), 10% citric acid (3×120 mL), saturated sodium bicarbonate (1×120 mL), and water (2×120 mL). The organic layer was dried with magnesium sulfate, filtered, and concentrated under reduce pressure before being chromatographed on silica gel eluting with a mixture of dichloromethane and ethyl acetate (65:35). The purification produced 815 mg (81.5%) of the desired material (14).

$^1$H NMR (in CDCl$_3$; 600 MHz): 7.42 (m, 5H, —CH$_2$CO$_2$CH$_2$C$_6$H$_5$), 6.96 (bs, 1H, —HNC(O)CH$_2$CH$_2$CO$_2$Bn), 5.36 (bs, 2H, BocHNCH$_2$CH(R)CH$_2$NHBoc), 5.17 (s, 2H, —CH$_2$CO$_2$CH$_2$C$_6$H$_5$), 3.80 (bs, 1H, BocHNCH$_2$CH(R)CH$_2$NHBoc), 3.36 (m, 2H, BocHNCH$_\alpha$CH(R)CHNHBoc), 3.20 (m, 2H, BocHNCH$_\beta$CH(NH$_2$)CH$_\beta$NHBoc), 2.75 (t, 2H, J=6.9 Hz, —HNC(O)CH$_2$CH$_2$CO$_2$CH$_2$C$_6$H$_5$), 2.52 (t, 2H, J=6.9 Hz, —HNC(O)CH$_2$CH$_2$CO$_2$CH$_2$C$_6$H$_5$), and 1.49 ppm (s, 18H, —NHCO$_2$C(CH$_3$)$_3$). $^{13}$C NMR (CDCl$_3$; 150 MHz): 173.05 (1C, —HNC(O)CH$_2$CH$_2$CO$_2$Bn), 172.24 (1C, —HNC(O)—CH$_2$CH$_2$CO$_2$Bn), 157.85 (2C, —HNCO$_2$C(CH$_3$)$_3$), 136.27 (1C, —CO$_2$CH$_2$C$_{1'arom}$), 128.97 (2C, H—C$_{2'arom}$ and H—C$_{6'arom}$), 128.66 (1C, H—C$_{4'arom}$), 128.64 (2C, H—C$_{3'arom}$ and H—C$_{5'arom}$), 80.24 (2C, —HNCO$_2$C(CH$_3$)$_3$), 66.91 (1C, —HNC(O)CH$_2$CH$_2$CO$_2$CH$_2$C$_6$H$_5$), 53.06 (1C, BocHNCH$_2$CH(R)CH$_2$NHBoc), 41.15 (2C, BocHNCH$_2$CH(R)CH$_2$NHBoc), 31.46 (1C, —HNC(O)CH$_2$CH$_2$CO$_2$CH$_2$C$_6$H$_5$), 29.97 (1C, —HNC(O)CH$_2$CH$_2$—CO$_2$CH$_2$C$_6$H$_5$), and 28.77 ppm (6C, —NHCO$_2$C(CH$_3$)$_3$). MS (m/z, EI): 481, 480 (w, M$^+$+1), 424, 414, 350, 306, 294, 293 (100%), 250, 249, 233, 224, 216, 215, 208, 193, 191, 160, 159, 149 (C$_6$H$_5$CH$_2$O$_2$CH$_2$$^+$), 133, and 91 (C$_6$H$_5$CH$_2$$^+$).

Methyl N-[2-[1,3-bis-(tert-butoxycarbonylamnino)]propyl]succinamate (15)

In a 25 mL flame-dried three necked, round-bottom flask equipped with an addition funnel, a septum, a stopper, and a magnetic stirring bar are placed mono-methyl succinamate (20) (459.3 mg; 3.5 mmole), 1-hydroxybenzotriazole hydrate (469.8 mg; 3.5 mmole), N,N-diisopropylethylamine (606 µL; 449.7 mg; 3.5 mmole), and dry ethyl acetate (10 mL). The resulting solution was cooled to 0° C. with an ice bath followed by addition of 3.48 mL (3.48 mmole) of 1M 1,3-dicyclohexylcarbodiimide in dichloromethane. The mixture was stirred for ten minutes under an atmosphere of argon before adding slowly a solution of N$^1$,N$^3$-bis(tert-butoxycarbonyl)-1,2,3-triaminopropane (13) (1.0001 g; 3.5 mmole) dissolved in 5 mL of dry ethyl acetate. After 23.8 hours at room temperature, the reaction mixture was filtered on celite. The filtrate was washed with a solution of 10% citric acid (3×100 mL), water (1×100 mL), sodium bicarbonate (1×100 mL), and finally saturated sodium chloride solution (2×100 mL). The organic layer was dried with magnesium sulfate, filtered, and concentrated under reduced pressure before being chromatographed on silica gel eluting with a mixture of dichloromethane and methanol (95:5). The purification produced 1072.5 mg (76.5%) of the desired material (15).

$^1$H NMR (CDCl$_3$; 600 MHz): 7.31 (bs, 1H, —HNCOCH$_2$CH$_2$CO$_2$CH$_3$), 5.39 (bs, 2H, BocNHCH$_2$CH(R)CH$_2$NHBoc), 3.83 (bs, 1H, BocHNCH$_2$CH(R)CH$_2$NHBoc), 3.72 (s, 3H, —CH$_2$CO$_2$CH$_3$), 3.38 (m, 2H, BocHNCH$_\alpha$CH(R)CH$_\alpha$NHBoc), 3.22 (m, 2H, BocHNCH$_\beta$CHCH$_\beta$NHBoc), 2.69 (t, 2H, J=6.9 Hz, —NHC(O)CH$_2$CH$_2$CO$_2$CH$_3$), 2.50 (t, 2H, J=6.9 Hz, —NHC(O)CH$_2$CH$_2$CO$_2$CH$_3$), and 1.48 ppm (s, 18H, —NHCO$_2$C(CH$_3$)$_3$). $^{13}$C NMR (CDCl$_3$; 150 MHz): 173.86 (1C, —NHC(O)CH$_2$CH$_2$CO$_2$CH$_3$), 172.51 (1C, —NHC(O)CH$_2$CH$_2$CO$_2$CH$_3$), 158.01 (1C, —NHCO$_2$C(CH$_3$)$_3$), 80.41 (3C, —HNCO$_2$—C(CH$_3$)$_3$), 53.17 (1C, BocHNCH$_2$CH(R)CH$_2$NHBoc), 52.38 (1C, —NHC(O)CH$_2$CH$_2$—CO$_2$CH3), 41.40 (2C, BocHNCH$_2$CH(R)CH$_2$NHBoc), 31.64 (1C, —NHCOCH$_2$CH$_2$—CO$_2$CH$_3$), 29.90 (1C, —NHCOCH$_2$—CH$_2$CO$_2$CH$_3$), and 28.95 ppm (6C, —NHCO$_2$C(CH$_3$)$_3$). MS (m/z, EI): 405 (M$^+$+1), 404 (M$^+$), 348, 274, 217 (M$^+$-[C(CH$_3$)$_3$]—[CH$_3$O$_2$CCH$_2$CH$_2$CONH—]), 173 (M$^+$-[CO$_2$C(CH$_3$)$_3$]—[CH$_3$O$_2$CCH$_2$—CH$_2$CONH—]), 159, 157 (M$^+$-[H$_2$NCO$_2$C(CH$_3$)$_3$]—[CH$_3$O$_2$CCH$_2$CH$_2$—CONH—]), 116, 115 (100%, CH$_3$O$_2$CCH$_2$CH$_2$CO—), 103, 59 (CH$_3$O$_2$C—), 57 ($^+$C(CH$_3$)$_3$), 55, and 41.

Benzyl N-[2-(1,3-diamino)propyl]succinamate dihydrochloride (16)

Benzyl N-[2[1,3-bis(tert-butyloxycarbonylamino)propyl]succinamate (14) (684.1 mg; 1.4 mmole) was treated at room temperature with 10 mL of a 1.0M hydrochloric acid solution in ethyl acetate for 75 minutes. An additional quantity (10 mL) of the acid solution was added while stirring at room temperature for another 3.25 hours. The white precipitate was filtered off the reaction mixture with a sintered glass funnel (fine porosity). The white solid was then dried under vacuum for several hours. The hydrolysis reaction produced 419 mg (83.4%) of the benzyl N-(1',3'-diamino-2'-propyl)succinamate dihydrochloride (16).

$^1$H NMR (CD$_3$OD; 600 MHz): 7.38 (m, 5H, —NHCOCH$_2$CH$_2$CO$_2$CH$_2$C$_6$H$_5$), 5.17 (s, 2H, —NHC(O)CH$_2$CH$_2$CO$_2$CH$_2$C$_6$H$_5$), 4.47 (tt, 1H, J=3.8 and 10.3 Hz, H$_3$$^+$NCH$_2$CH(R)—CH$_2$N$^+$H$_3$), 3.28 (dd, 2H, J=3.8 and 13.2 Hz, H$_2$NCH$_\alpha$CH(R)CH$_\alpha$NH$_2$), 3.14 (dd, 2H, J=10.3 and 13.2 Hz, H$_2$NCH$_\beta$CH(R)—CH$_\beta$NH$_2$), 2.79 (t, 2H, J=6.7 Hz, —NHCOCH$_2$—CH$_2$CO$_2$CH$_2$C$_6$H$_5$), and 2.66 ppm (t, 2H, J=6.7 Hz, —NHCOCH$_2$CH$_2$CO$_2$CH$_2$C$_6$H$_5$). $^{13}$C NMR (CD$_3$OD; 150 MHz): 175.09 (1C, —HN(O)CCH$_2$CH$_2$CO$_2$Bn), 174.22 (1C, —HN(O)CCH$_2$CH$_2$CO$_2$Bn), 136.36 (1C, —CO$_2$CH$_2$—C$_{1'arom}$), 128.59 (2C, H—C$_{3'arom}$ and H—C$_{5'arom}$), 128.31 (1C, H—C$_{4'arom}$), 128.18 (2C, H—$\underline{C}_{2'arom}$ and H—$\underline{C}_{6'arom}$), 66.76 (1C, —HNC(O)CH$_2$CH$_2$CO$_2\underline{C}$H$_2$C$_6$H$_5$), 46.42 (1C, H$_2$NCH$_2$$\underline{C}$H(R)CH$_2$NH$_2$), 41.08 (2C, H$_2$N$\underline{C}$H$_2$CH(R)$\underline{C}$H$_2$NH$_2$), 30.50 (1C, —HNC(O)$\underline{C}$H$_2$CH$_2$CO$_2$CH$_2$C$_6$H$_5$), and 29.07 ppm (1C, —HNC(O)CH$_2$$\underline{C}$H$_2$CO$_2$CH$_2$C$_6$H$_5$). MS (m/z, EI): 281 (M$^+$+2H$^+$), 280 (M$^+$+H$^+$), 262, 249, 233, 232, 231, 132 (M$^+$+2-[C$_6$H$_5$CH$_2$O$_2$CCH$_2$]), 108, 107 (C$_6$H$_5$CH$_2$O$^+$), 91 (100%, C$_6$H$_5$CH$_2$$^+$), 79, and 72.

N$^1$,N$^1$,N$^3$,N$^3$-tetra[2'-(tert-butoxycarbonyl)ethyl]-1,3-diamino-2-propanol (17)

A mixture of 1,3-diamino-2-propanol (2.023 g; 22.4 mmole) and tert-butyl acrylate (24 mL; 21.192 g; 165.3 mmole) was heated at reflux with stirring, and under an atmosphere of argon, for a period of 6 days. The reaction mixture was then cooled and concentrated under reduced pressure. Purification by flash chromatography using a mixture of dichloromethane and methanol (96:4) as eluent gave 11.51 g (85%) of the desired product (17) as a yellow oil.

Benzyl N-[2-[N$^1$,N$^1$,N$^3$,N$^3$-tetra[2'-(tert-butoxycarbonyl)ethyl]-1,3-diaminopropyl]]succinamate (18)

N,N-Diisopropylethylamine (728 μL; 540.2 mg; 4.2 mmole) was added to a suspension of benzyl N-(1',3'-diamino-2'-propyl)succinamate dihydrochloride (16; 1 mmole) in dry tetrahydrofuran (20 mL). This mixture was stirred at room temperature until all the material has been dissolved. Tert-butyl acrylate (850 μL; 750.6 mg; 5.9 mmole) was then added and the solution was heated at reflux for 68.7 hours. The excess reagents were removed under reduced pressure and the obtained residue was purified by flash chromatography on a silica gel column. The product was eluted with a mixture of dichloromethane and methanol (85:15). The collected fractions were analyzed and the ones containing the desired product were combined and concentrated under vacuum. The purification produced 790 mg (95.5%) of benzyl N-[2-[N$^1$,N$^1$,N$^3$,N$^3$-tetra[2'-(tert-butoxycarbonyl)ethyl]-1,3-diaminopropyl]] (18) succinamate as a hygroscopic yellow solid.

Mono-benzyl Succinate (19)

A mixture of succinic anhydride (8.06 g; 80.5 mmole) and benzyl alcohol (10 mL; 10.45 g; 96.6 mmole) was shaken vigorously while heated at reflux with a steam bath until all the succinic anhydride has been dissolved (a period of about 32 minutes). The flask was then immerse in the steam bath and the mixture was heated at reflux for an additional 60 minutes. The excess of benzyl alcohol was removed under reduced pressure and the residue was cooled with an ice bath. The white precipitate was filtered off and triturated with water. The solid was dried under vacuum until constant weight. Thus, mono-benzyl succinate (19) was recovered in an excellent yield of 97.8% (16.396 g).

$^1$H NMR (in CDCl$_3$; 400 MHz): 7.36 (m, 5H, C$_6$$\underline{H}_5$CH$_2$O$_2$CCH$_2$CH$_2$CO$_2$H), 5.16 (s, 2H, C$_6$H$_5$C$\underline{H}_2$O$_2$CCH$_2$CH$_2$CO$_2$H), 2.70 ppm (m, 4H, C$_6$H$_5$CH$_2$O$_2$CC$\underline{H}_2$C$\underline{H}_2$CO$_2$H). $^{13}$C NMR (in CDCl$_3$; 100 MHz): 178.66 (1C, C$_6$H$_5$CH$_2$O$_2$CCH$_2$CH$_2$$\underline{C}$O$_2$H), 172.39 (1C, C$_6$H$_5$CH$_2$—O$_2$$\underline{C}$CH$_2$CH$_2$CO$_2$H), 136.08 (1C, CO$_2$CH$_2$—$\underline{C}_{1'arom}$), 129.00 (2C, H—$\underline{C}_{3'arom}$ and H—$\underline{C}_{5'arom}$), 128.72 (1C, H—$\underline{C}_{4'arom}$), 128.63 (2C, H—$\underline{C}_{2'arom}$ and H—$\underline{C}_{6'arom}$), 67.08 (1C, C$_6$H$_5$$\underline{C}$H$_2$O$_2$C—CH$_2$CH$_2$CO$_2$H), 29.32 (1C, C$_6$H$_5$CH$_2$O$_2$CCH$_2$$\underline{C}$H$_2$CO$_2$H), and 29.29 ppm (1C, C$_6$H$_5$CH$_2$O$_2$C$\underline{C}$H$_2$CH$_2$CO$_2$H).

Mono-methyl Succinate (20)

A mixture of succinic anhydride (80.02 g; 799.6 mmole) and dry methanol (38.9 mL; 30.77 g; 960.4 mmole) was shaken vigorously while heated at reflux with a steam bath until all the succinic anhydride had been dissolved (a period of about 18 minutes). The flask was then immerse in the steam bath and the mixture was heated at reflux for an additional 25 minutes. The excess of methanol was removed under reduced pressure and the residue was cooled with an ice bath. The white precipitate was filtered off and triturated with water. The solid was dried under vacuum until constant weight. Thus, mono-methyl succinate (20) was recovered in an excellent yield of 93.6% (98.886 g).

$^1$H NMR (in CDCl$_3$; 400 MHz): 3.71 (s, 3H, C$\underline{H}_3$O$_2$CCH$_2$CH$_2$CO$_2$H), 2.71 (dd, 1H, J=2.1 and 5.8 Hz, CH$_3$O$_2$CC$\underline{H}_\alpha$CH$_2$CO$_2$H), 2.69 (dd, 1H, J=1.2 and 5.7 Hz, CH$_3$O$_2$C—C$\underline{H}_\beta$CH$_2$CO$_2$H), 2.65 (dd, 1H, J=1.1 and 5.6 Hz, CH$_3$O$_2$CCH$_2$C$\underline{H}_\alpha$CO$_2$H), and 2.63 ppm (dd, 1H, J=2.1 and 5.8 Hz, CH$_3$O$_2$CCH$_2$C$\underline{H}_\beta$CO$_2$H). $^{13}$C NMR (in CDCl$_3$; 100 MHz): 178.75 (1C, CH$_3$O$_2$CCH$_2$CH$_2$$\underline{C}$O$_2$H), 173.04 (1C, CH$_3$O$_2$$\underline{C}$CH$_2$CH$_2$CO$_2$H), 52.40 (1C, $\underline{C}$H$_3$O$_2$CCH$_2$CH$_2$CO$_2$H), 29.33 (1C, CH$_3$O$_2$CCH$_2$$\underline{C}$H$_2$CO$_2$H), and 29.02 ppm (CH$_3$O$_2$C—$\underline{C}$H$_2$CH$_2$CO$_2$H). Melting Point: 55.5 to 57° C.

EXAMPLE 4

Synthesis of a trisaminopropane bis-[2'-hydroxybenzyl]dihydroxamic acid chelator (HBTDHA)

N$^1$,N$^3$-[bis(2'-hydroxybenzylidene)]-1,3-diamino-2-propanol (21)

Salicylaldehyde (13.6125 g; 111.5 mmole) and benzene (60 mL) are placed in a 200 mL round bottom flask equipped with a Dean-Stark and a condenser. 1,3-diamino-2-propanol (5.0232 g; 55.7 mmole) and an additional quantity of benzene are added with stirring. The reaction mixture was then heated to reflux for 23.4 hours. A yellow solid precipitate upon cooling the mixture. The desired compound was obtained after filtration and washing with benzene. The reaction produced 14.987 g (90.1%) of N$^1$,N$^3$-bis(2'-hydroxybenzylidene)-1,3-diamino-2-propanol (21) after drying under vacuum.

$^1$H NMR (CDCl$_3$; 400 MHz): 8.41 (s, 2H, HOC$_6$H$_4$C$\underline{H}$=N—), 7.33 (ddd, 2H, J=1.7, 7.3 and 8.3 Hz, $\underline{H}$—C$_{4'arom}$), 7.30 (dd, 2H, J=1.7 and 7.6 Hz, $\underline{H}$—C$_{6'arom}$), 6.97 (dt, J=0.5 and 8.3 Hz, $\underline{H}$—C$_{3'arom}$), 6.90 (tt, 2H, J=0.5 and 7.6 Hz, $\underline{H}$—C$_{5'arom}$), 4.29 (U, 1H, J=4.5 and 6.6 Hz, HOC$_6$H$_4$CH=NCH$_2$C$\underline{H}$(OH)CH$_2$N=CHC$_6$H$_4$OH), 3.88 (ddd, 2H, J=1.2, 4.5, and 12.4 Hz, HOC$_6$H$_4$CH=NC$\underline{H}_\alpha$CH(OH)C$\underline{H}_\alpha$N=CHC$_6$H$_4$OH), and 3.73 ppm (ddd, 2H, J=0.9, 6.7, and 12.4 Hz, HOC$_6$H$_4$CH=NC$\underline{H}_\beta$CH(OH)C$\underline{H}_\beta$N=CHC$_6$H$_4$OH). $^{13}$C NMR (CDCl$_3$; 100 MHz): 167.90 (HOC$_6$H$_4$—$\underline{C}$H=NCH$_2$CH(OH)CH$_2$N=$\underline{C}$HC$_6$H$_4$OH), 161.44 (HO—$\underline{C}_{2'arom}$), 133.06 (H—$\underline{C}_{4'arom}$), 132.03 (H—$\underline{C}_{6'arom}$), 119.24 (H—$\underline{C}_{5'arom}$), 119.06 (R—N=CH—$\underline{C}_{1'arom}$), 117.45 (H—$\underline{C}_{3'arom}$), 70.91 (HOC$_6$H$_4$CH=NCH$_2$$\underline{C}$H(OH)CH$_2$N=CH—C$_6$H$_4$OH), 63.66 ppm (HOC$_6$H$_4$CH=N$\underline{C}$H$_2$CH(OH)$\underline{C}$H$_2$N=CHC$_6$H$_4$OH). MS (m/z, EI): 299, 298, 165, 164 (100%), 135, 134, 107, and 77.

$N^1,N^3$-[bis(2'-hydroxybenzyl)]-1,3-diamino-2-propanol (22)

A solution of $N^1,N^3$-bis-(2'-hydroxybenzylidene)-1,3-diamino-2-propanol (21) (4.0878 g; 13.7 mmole) in methanol (120 mL) was poured into a Parr hydrogenation bottle. Palladium on charcoal (10%; 133.6 mg) was added to the solution and the resulting mixture was placed in a Parr hydrogenation apparatus. The mixture was degassed under reduced pressure followed by the introduction of a hydrogen atmosphere (40 psi). The reaction was vigorously shaken for 27.25 hours and the hydrogen was removed in vacuo. The catalyst was then filtered off over celite and the filtrate was concentrated by rotatory evaporation and dried under reduced pressure to give an off-white fluffy solid (3.91 g). The crude material was purified by flash chromatography using a mixture of dichloromethane, methanol, and ammonium hydroxide (84/15/1) as eluent. The fractions containing the desired substance were combined and the solvents were removed under vacuum to give 3.572 g (86.2%) of $N^1,N^3$-bis(2'-hydroxybenzyl)-1,3-diamino-2-propanol (22).

$^1$H NMR (CDCl$_3$; 600 MHz): 7.31 (t, 2H, J=8.0 Hz, H—C$_{4'arom}$), 7.20 (d, 2H, J=7.4 Hz, H—C$_{6'arom}$), 6.86 (d, 2H, J=8.0 Hz, H—C$_{3'arom}$), 6.82 (t, 2H, J 7.4 Hz, H—C$_{5'arom}$), 6.08 (bs, 5H, —OH(arom. and aliph.) and —NH), 4.03 (m, 1H, C$_6$H$_4$(OH)CH$_2$HNCH$_2$CH(OH)—CH$_2$NHCH$_2$C$_6$H$_4$(OH)), 4.03 (d, 2H, J=13.8 Hz, C$_6$H$_4$(OH)CH$_\alpha$NHCH$_2$CH(OH)CH$_2$NHCH$_\alpha$C$_6$H$_4$(OH)), 3.99 (d, 2H, J=13.8 Hz, C$_6$H$_4$(OH)CH$_\beta$HNCH$_2$CH(OH)—CH$_2$NHCH$_\beta$C$_6$H$_4$(OH)), 2.71 (dd, 2H, J=3.3 and 12.3 Hz, C$_6$H$_4$(OH)CH$_2$HN—CH$_\alpha$CH(OH)CH$_\alpha$NHCH$_2$C$_6$H$_4$(OH)), 2.67 ppm (dd, 2H, J=8.2 and 12.3 Hz, C$_6$H$_4$(OH)—CH$_2$HNCH$_\beta$CH(OH)CH$_\beta$NHCH$_2$C$_6$H$_4$(OH)). $^{13}$C NMR (CDCl$_3$; 150 MHz): 158.28 (2C, HO—C$_{2'arom}$)), 129.53 (2C, H—C$_{6'arom}$), 129.21 (2C, H—C$_{4'arom}$), 112.29 (2C, —HNCH$_2$—C$_{1'arom}$), 119.67 (2C, H—C$_{5'arom}$), 116.89 (2C, H—C$_{3'arom}$), 69.05 (1C, —HNCH$_2$CH(OH)—CH$_2$NH), 52.66 (2C, —HNCH$_2$CH(OH)CH$_2$NH—), and 52.44 ppm (2C, C$_6$H$_5$CH$_2$NH—). MS (m/z, EI): 304 (M$^+$+2), 303 (M$^+$+1), 162, 136, 123, 122 (HO—C$_6$H$_4$CH$_2$NH$^+$), 107 (100%, HOC$_6$H$_4$CH$_2$$^+$), 77, 56, and 44. FT-IR (CDCl$_3$, NaCl cells): 3650 to 2600 (bs, N—H, H—O (phenol, alkyl), C—H$_{arom}$, CH$_{aliph}$) 1817, 1794, 1701, 1256, 1187, 1152, 1104, 1036, 1015, and 890 cm$^{-1}$.

$N^1,N^3$-[bis(2'-hydroxybenzyl)]-$N^1,N^3$-[bis[2-[N'-methyl,N'-(tert-butyldiphenylsilyl-oxy)aminocarbonyl]ethyl]]-1,3-diamino-2-propanol (23)

To a solution of N-methyl,N-(tert-butyldiphenylsilyloxy)acrylamide (28) (723.1 mg, 2.1 mmole) in 30 mL of tetrahydrofuran, $N^1,N^3$-bis-(2'-hydroxybenzyl)-1,3-diamino-2-propanol (22) (254.7 mg; 0.8 mmole) was added. The resulting solution was stirred and heated at reflux for 46.7 hours. The volatile substances were removed under reduced pressure after cooling the reaction mixture. The residue (1.1 g of a yellow oil) was purified by flash chromatography using a mixture of dichloromethane, methanol, and N,N-diisopropylethylamine (79.8/20/0.2) to elute the desired bishydroxamate. The fractions containing the product were combined and the solvents were eliminated under vacuum. 596.7 mg (72.2%) of $N^1,N^3$-[bis(2'-hydroxybenzyl)]-$N^1,N^3$-[bis[2-[N'-methyl,N'-(tert-butyldiphenylsilyloxy)aminocarbonyl]ethyl]]1,3-diamino-2-propanol (23) as a colorless oil was obtained after the purification.

$^1$H NMR (CDCl$_3$; 600 MHz): 7.68 (d, 8H, J=6.9 Hz, H—C$_{3'',4''\&5''arom}$ of —OSi(Ph)$_2$t-Bu), 7.42 (m, 12H, H—C$_{2''\&6''arom}$ of —OSi(Ph)$_2$t-Bu), 7.20 (t, 2H, J=7.3 Hz, H—C$_{4'arom}$), 6.92 (d, 2H, J=7.2 Hz, H—C$_{6'arom}$), 6.86 (d, 2H, J=8.1 Hz, H—C$_{3'arom}$), 6.79 (t, 2H, J=7.3 Hz, H—C$_{5'arom}$), 4.11 (bs, 1H, —HNCH$_2$CH(OH)CH$_2$NH—), 3.60 (m, 4H), 3.17 (s, 6H, —CON(CH$_3$)OTBDPS), 2.55 (m, 11H), 1.60 (m, 2H), 1.49 (d, 1H, J=6.7 Hz), and 1.18 ppm (s, 18H, —OSi(Ph)$_2$C(CH$_3$)$_3$). $^{13}$C NMR (CDCl$_3$; 150 MHz): 158.16 (2C, HO—C$_{2'arom}$), 136.75, 136.70 (8C, H—C$_{3'arom}$ and H—C$_{5'arom}$ of —OSi(Ph)$_2$t-Bu), 135.41, 131.18 (4C, H—C$_{4''arom}$ of —OSi(Ph)$_2$tBu), 130.24, 129.44 (2C, H—C$_{6'arom}$), 128.48 (8C, H—C$_{2''arom}$ and H—C$_{6''arom}$ of —OSi(Ph)$_2$t-Bu), 128.32(2C, H—C$_{4'arom}$), 119.68 (2C, H—C$_{5'arom}$), 117.01 (2C, H—C$_{3'arom}$), 58.57 (—N(R)CH$_2$CH(OH)CH$_2$N(R)—), 54.20, 49.28, 42.47, 38.00 (2C, —CON(CH$_3$)OTBDPS), 30.33, 27.53 (6C, —OSi(Ph)$_2$C(CH$_3$)$_3$), 27.17, 19.74 (2C, —OSi(Ph)$_2$C(CH$_3$)$_3$), 19.26, and 18.00 ppm. MS (m/z, ES): 1004.4 (M$^+$+Na), 1003.8 (M$^+$−1+Na), 982.6 (M$^+$+1), 981.6 (M$^+$), 743.6 (M$^+$+1-[(CH$_3$)$_3$CSi(Ph)$_2$]), 505.3, 491.4 (100%; M$^{2+}$+1), and 372.4, 207.0, and 202.0. FT-IR (CDCl$_3$, NaCl cells): 3395 (bs, H—O), 3048, 2955, 2931, 2861, 1737, 1661, 1490, 1425, 1255, 1114, 820, 738, and 703 cm$^{-1}$.

Benzyl N-[2-[$N^1,N^3$-bis(2-hydroxybenzylidene)]-1,3-diaminopropyl]succinamate (24)

Benzyl N-(1',3'-diamino-2'-propyl)succinamate dihydrochloride (16) (1.3 mmole) was placed in a 50 mL round bottom flask. Benzene (25 mL), dichloromethane (4 mL), and finally N,N-diisopropylethylamine (1.85 mL; 10.6 mmole) were added to the crude diamine hydrochloride salt. The mixture was stirred several minutes at room temperature and the flask was equipped with a Dean-Stark and a condenser. Salicylaldehyde (320 μL; 366.7 mg; 3.0 mmole) was added to the mixture. The reaction was heated at reflux for 71.3 hours after which the solvents were removed under reduced pressure. Thus, the yellow obtained solid was purified by flash chromatography on silica gel using a mixture of dichloromethane and ethyl acetate (70:30) to elute the desired compound. The purification produced 378 mg (58.5%) of benzyl N-[2-[$N^1,N^3$-bis(2'-hydroxybenzylidene)]-1,3-diaminopropyl]succinamate (24) as a yellow oil.

Benzyl N-[2-[$N^1,N^3$-bis(2'-hydroxybenzyl)]-1,3-diaminopropyl]succinamate (25)

Benzyl N-[2-[$N^1,N^3$-bis(2'-hydroxybenzylidene)]-1,3-diaminopropyl]succinamate (24) (312.9 mg; 0.6 mmole) was dissolved with a mixture of ethanol (10 mL) and tetrahydrofuran (10 mL) and sodium borohydride (56.7 mg; 1.5 mmole) was added slowly. The reaction mixture was stirred at room temperature for 2.5 hours. Water (10 mL) was added and the resulting mixture was concentrated under reduced pressure. Dichloromethane (50 mL) and water (50 mL) were added to the obtained residue and the two layers were separated. The water solution was extracted two times with dichloromethane and the organic layers were combined. The solvent was evaporated under vacuum and the residue was purified by flash chromatography (dichloromethane/methanol/ammonium hydroxide; 84.8/15/0.2). 128 mg (40.5%) of benzyl N-[2-[$N^1,N^3$-bis(2'-hydroxybenzyl)]-1,3-diaminopropyl]succinamate (25) was recovered after the purification.

$^1$H NMR (CDCl$_3$; 600 MHz): 7.03 (m, 1H), 7.01 (d, 2H, J=6.7 Hz), 6.83 (dt, 2H, J=1.1 and 8.6 Hz), 6.81 (dd, 2H, J=1.1 and 7.4 Hz), 4.47 (m, 3H, —HNCH$_2$C$\underline{H}$(R)CH$_2$NH— and —NHCOCH$_2$CH$_2$CO$_2$C$\underline{H}_2$C$_6$H$_5$), 4.13 (d, 2H, J=13.7 Hz, HOC$_6$H$_5$C$\underline{H}_\alpha$NH—), 3.87 (d, 2H, J=13.7 Hz, HOC$_6$H$_5$C$\underline{H}_\beta$NH—), 3.33 (m, 2H, —HNC$\underline{H}_\alpha$CH(R)C$\underline{H}_\alpha$NH—), 2.95 (dd, 2H, J=4.1 and 12.7 Hz, —HNC$\underline{H}_\beta$CH(R)C$\underline{H}_\beta$NH—), and 2.82 ppm (s, 4H, —NHCOC$\underline{H}_2$—C$\underline{H}_2$CO$_2$CH$_2$C$_6$H$_5$).

Benzyl N-[2-[N$^1$,N$^3$-bis(2'-hydroxybenzyl)]-N$^1$,N$^3$-[bis[2-[N'-methyl,N'-(tert-butyl-diphenylsilyloxy)]aminocarbonyl]ethyl]]-1,3-diaminopropyl]succinamate (26)

To a solution of N-methyl,N-(tert-butyldiphenylsilyloxy)acrylamide (28) (280 mg, 0.8 mmole) and N,N-diisopropylethylamine (110 µL; 81.6 mg; 0.6 mmole) in 15 mL of tetrahydrofuran, benzyl N-[2-[N$^1$,N$^3$-bis(2'-hydroxybenzyl)]-1,3-diaminopropyl]succinamate (25) (127.7 mg; 0.3 mmole) is added. The resulting solution is stirred and heated at reflux. The volatile substances are removed under reduced pressure after cooling the reaction mixture.

EXAMPLE 5

Hydroxylamine Derivatives
N-Methyl,N-(tert-butyldiphenylsilyl)hydroxylamine (27)

To a suspension of N-methyl hydroxylamine hydrochloride (9.0611 g; 108.5 mmole) in dry dichloromethane (100 mL) was added tert-butyldiphenylsilyl chloride (28.2 mL; 29.8074 g; 108.4 mmole) and N,N-diisopropylethylamine (47.5 mL; 35.245 g; 272.7 mmole). The reaction mixture was stirred at room temperature for 65.5 hours followed by the addition of water (200 mL). The two layers were separated and the aqueous layer was extracted twice (500 mL each) with methylene chloride. The organic solutions were then combined, dried with magnesium sulfate, filtered, and concentrated to dryness under reduces pressure. A yellow liquid (31.65 g) was isolated from the reaction mixture and purified by liquid chromatography on silica gel using a mixture of hexane and ethyl acetate (85:15) to elute the desired product. The purification process gave 29.46 g (95.1%) of N-Methyl,N-(tert-butyldiphenylsilyl)hydroxylamine (27) as a colorless oil.

$^1$H NMR (CDCl$_3$; 300 MHz): 7.74 (dd, 4H, J=1.7 and 7.7 Hz, $\underline{H}$—C$_{2'arom}$ and $\underline{H}$—C$_{6'arom}$), 7.4 (m, 6H, $\underline{H}$—C$_{3'arom}$, $\underline{H}$—C$_{4'arom}$ and $\underline{H}$—C$_{5'arom}$), 2.70 (s, 3H, t-(CH$_3$)$_3$CSi(Ph)$_2$ONHC$\underline{H}_3$), and 1.11 ppm (s, 9H, , t-(CH$_3$)$_3$CSi(Ph)$_2$ONHC$\underline{H}_3$). $^{13}$C NMR (CDCl$_3$; 100 MHz): 136.05 (4C, H—$\underline{C}_{3'arom}$ and H—$\underline{C}_{5'arom}$), 134.26 (2C, —O(t-Bu)Si—$\underline{C}_{1'arom}$), 130.00 (2C, H—$\underline{C}_{4'arom}$), 127.99 (4C, H—$\underline{C}_{2'arom}$ and H—$\underline{C}_{6'arom}$), 41.96 (1C, $\underline{C}$H$_3$NHOTBDPS), 27.75 (3C, —OSi(Ph)$_2$C($\underline{C}$H$_3$)$_3$), and 19.56 ppm (1C,—OSi(Ph)$_2$$\underline{C}$(CH$_3$)$_3$). MS (m/z, EI): 286 (M$^+$), 229, 228 (100%), 208, 199, and 197. FT-IR (CDCl$_3$, NaCl cells): 3268 (w, N—H), 3070, 3048, 2956, 2932, 2894, 2857, 1472, 1428, 1391, 1113, 871, 823, 739, 701, and 1824 cm.

N-Methyl,N-(tert-butyldiphenylsilyloxy)acrylamide (28)

N-Methyl,N-(tert-butyldiphenylsilyl)hydroxylamine (27) (10.0322 g; 35.1 mmole) was placed in a flame dried 500 mL round bottom flask. Dry dichloromethane (50 mL) was added to dissolved the hydroxylamine derivative followed by the addition of N,N-diisopropylethylamine (16 mL; 11.87 g; 91.9 mmole). The resulting solution was stirred and cooled at 0° C. with an ice bath. Acryloyl chloride (2.8 mL; 3.1192 g; 34.5 mmole) in 10 mL of dry dichloromethane was slowly added to the mixture while its temperature was kept at 0° C. for about two hours. The reaction warmed up slowly and left alone for about 48 hours. Water (200 mL) was added to the reaction and the two layers were separated. The organic layer was washed successively with 10% ammonium chloride (3×200 mL), saturated bicarbonate solution (3×200 mL), and brine (2×200 mL). The organic solution was then dried with magnesium sulfate, filtered, and the solvent evaporated under reduced pressure to give 12.16 g of a yellow oil. The crude product was purified by flash chromatography (silica gel) using a mixture of hexane and ethyl acetate (80:20) to elute the compound. Fractions were analyzed and the ones containing the desired product were combined and the solvents were removed under vacuum. The purification produced 10.08 g (84.5%) of N-Methyl,N-(tert-butyldiphenylsilyloxy)acrylamide (28) as a colorless oil.

$^1$H NMR (CDCl$_3$; 500 MHz): 7.69 (d, 4H, J=7.9 Hz, $\underline{H}$—C$_{6'arom}$ and $\underline{H}$—C$_{2'arom}$) 7.46 (t, 2H, J=7.4 Hz, $\underline{H}$—C$_{4'arom}$), 7.39 (t, 4H, J=7.4 Hz, $\underline{H}$—C$_{3'arom}$ and $\underline{H}$—C$_{5'arom}$), 6.70 (m, 1H, $\underline{H}_2$C=CH—CO—N(CH$_3$)OTBDPS), 6.17 (dd, 1H, J=1.9 and 17.1 Hz, $\underline{H}_{trans}$C=CH—CON(CH$_3$)OTBDPS), 5.54 (dd, 1H, J=2.0 and 10.4 Hz, $\underline{H}_{cis}$C=CH—CO—N(CH$_3$)OTBDPS), 3.14 (s, 3H, t-(CH$_3$)$_3$CSi(Ph)$_2$O—NRC$\underline{H}_3$), 1.17 ppm (s, 9H, t-(C$\underline{H}_3$)$_3$CSi(Ph)$_2$O—NRCH$_3$). $^{13}$C NMR (CDCl$_3$; 100 MHz): 165.00 (1C, CH$_2$=CHCON—), 136.51 (4C, H—$\underline{C}_{3'arom}$ and H—$\underline{C}_{5'arom}$), 131.79 (2C, —O(t-Bu)Si—C$_{1'arom}$), 130.91 (2C, H—$\underline{C}_{4'arom}$), 128.40 (1C, $\underline{C}$H$_2$=CHCON—), 128.23 (4C, H—$\underline{C}_{2'arom}$ and H—$\underline{C}_{6'arom}$), 127.12 (1C, CH$_2$=$\underline{C}$HCON), 35.50 (1C, $\underline{C}$H$_3$N(R)OTBDPS), 27.41 (3C, —OSi(Ph)$_2$C($\underline{C}$H$_3$)$_3$), and 19.75 (1C, —OSi(Ph)$_2$$\underline{C}$(CH$_3$)$_3$). MS (m/z, EI): 340 (w, M$^+$), 283, 282 (100%, M$^+$-(CH$_3$)$_3$CH), 199, 135, and 68.

N-benzyloxyacrylamide (30)

A solution of acryloyl chloride (3 mL; 3.342 g; 36.9 mmole) dissolved in dry dichloromethane (25 mL) was cooled at 0° C. with an ice bath. A mixture of O-benzyl hydroxylamine hydrochloride (6.4902 g; 40.66 mmole) and N,N-diisopropylethylamine (15.6 mL; 11.575 g; 89.56 mmole) in dry dichloromethane (110 mL) was slowly added over a period of 1 hour to the cooled solution. Next, the ice bath was removed, and the reaction mixture was left stirring overnight while its temperature warmed up gradually to room temperature. Water (250 mL) was added to the reaction and the layers were separated. The organic solution was washed with diluted hydrochloric acid (0.2N; 3×300 mL), a saturated sodium bicarbonate solution (1×200 mL), water (3×250 mL), and finally brine (1×250 mL). The organic layer was then dried over magnesium sulfate, filtered, and the solvent removed under reduced pressure. The residue was purified by flash chromatography using a mixture of hexane and ethyl acetate (70:30) to elute the product. The purification gave 3.165 g (48.4%) of N-benzyloxyacrylamide (30) as a viscous colorless oil. $^1$H NMR (CDCl$_3$; 300 MHz): 8.27 (bs, 1H, C$_6$H$_5$CH$_2$ON$\underline{H}$COCH=CH$_2$), 7.39 (s, 5H, C$_6$$\underline{H}_5$CH$_2$ONHCOCH=CH$_2$), 6.41 (d, 1H, J=16.6 Hz, C$_6$H$_5$CH$_2$ONHCOCH=C$\underline{H}_{trans}$), 6.02 (m, 1H, C$_6$H$_5$CH$_2$ON$\underline{H}$COCH=CH$_2$), 5.72 (d, 1H, J=9.5 Hz, C$_6$H$_5$CH$_2$ONHCOCH=C$\underline{H}_{cis}$), 4.93 ppm (bs, 2H, C$_6$H$_5$C$\underline{H}_2$ONHCOCH=CH$_2$).

O-benzylhydroxylamine (29)

Commercially available from Sigma-Aldrich Canada Ltd. (Oakville, Ontario).

$^1$H NMR (CDCl$_3$; 300 MHz): 7.36 (m, 5H, C$_6$H$_5$CH$_2$ONH$_2$), 5.40 (bs, 2H, C$_6$H$_5$CH$_2$ONH$_2$), 4.70 ppm (s, 2H, C$_6$H$_5$CH$_2$ONH$_2$).

N-(tert-butoxycarbonyl),N-(tert-butoxycarbonyloxy) acrylamide (32)

A solution of acryloyl chloride (700 µL; 779.8 mg; 8.6 mmole) dissolved in dry dichloromethane (20 mL) was cooled at 0° C. with an ice bath. A mixture of tert-butyl N-(tert-butoxycarbonyloxy)carbamate (31) (2.0038 g; 8.6 mmole) and triethylamine (1.32 mL; 958.3 mg; 9.5 mmole) in dry dichloromethane (20 mL) was slowly added over a period of 1 hour to the cooled solution. The ice bath was removed after 4 hours and the reaction mixture was left stirring overnight while its temperature warmed up gradually to room temperature. Water (100 mL) was added to the reaction and the layers were separated. The organic solution was washed with a 10% ammonium chloride solution (3×80 mL), water (2×100 mL), and finally brine (1×100 mL). The organic layer was then dried over magnesium sulfate, filtered, and the solvent removed under reduced pressure. The residue was purified by flash chromatography using a mixture of hexane and ethyl acetate (90:10) to elute the product. The purification gave 690 mg (28%) of N-(tert-butoxycarbonyl),N-(tert-butoxycarbonyloxy)acrylamide (32) as a colorless oil.

$^1$H NMR (CDCl$_3$; 300 MHz): 7.10 (dd, 1H, J=10.5 and 17.0 Hz, BocON(Boc)—COCH=CH$_2$), 6.50 (dd, 1H, J=1.5 and 17.0 Hz, BocON(Boc)COCH=CH$_{trans}$), 5.85 (dd, 1H, J=1.6 and 10.5 Hz, BocON(Boc)COCH=CH$_{cis}$), 1.55 and 1.54 ppm (2s, 18H, —CO$_2$C(CH$_3$)$_3$). $^{13}$C NMR (CDCl$_3$; 75 MHz): 162.87 (H$_2$C=CHC(O)N(Boc)OBoc), 151.2 (—CO$_2$C(CH$_3$)$_3$), 149.6 (—CO$_2$C(CH$_3$)$_3$), 131.0 (H$_2$C=CHC(O)N(Boc)OBoc), 128.6 (H$_2$C=CHC(O)N(Boc)OBoc), 86.1 (—CO$_2$C(CH$_3$)$_3$), 85.6 (—CO$_2$C(CH$_3$)$_3$), 27.9 (—CO$_2$C(CH$_3$)$_3$), and 27.5 ppm (—CO$_2$C(CH$_3$)$_3$). IR (neat, NaCl disks): 2980 (C—H), 2935 (C—H), 1790 (C=O), 1750 (C=O), 1710 (C=O), 1615, 1475, 1455, 1395, 1365, 1300, 1250, 1150, 1120, 1025, 960, 870, 835, and 745 cm$^{-1}$.

EXAMPLE 6

Examples of Labeling Experiment

N$^1$,N$^3$-[bis(2'-hydroxybenzyl)]-N$^1$,N$^3$-[bis[2-[N'-methyl,N'-(hydroxy)aminocarbonyl]ethyl]-1,3-diamino-2-propanol dihydrochloride (33)

To a solution of N$^1$,N$^3$-[bis(2'-hydroxybenzyl)]-N$^1$,N$^3$-[bis[2-[N'-methyl,N'-(tert-butyldiphenylsilyloxy)aminocarbonyl]ethyl]]-1,3-diamino-2-propanol (23) (22.8 mg; 23.2 µmole) solubilized in iso-propanol (3.46 mL) was added concentrated hydrochloric acid (0.54 mL; final concentration of 5.8%). This mixture was stirred at room temperature for 18.5 hours (the course of the reaction was followed by HPLC). The reaction mixture was then lyophilized to give a colorless oil. The crude residue was dissolved in a mixture of acetonitrile (2 mL) and water (1 mL). The resulting solution was used for the labeling experiments.

$^{67}$Gallium Labeling of N$^1$,N$^3$-[bis(2'-hydroxybenzyl)]-N$^1$,N$^3$-[bis[2-[N'-methyl,N'-(hydroxy)aminocarbonyl]ethyl]-1,3-diamino-2-propanol dihydrochloride (33)

a) at pH 6.6

A solution of the bis-(2-hydroxybenzyl)bis-hydroxamic acid (33) (200 µL; ~4 µg/µL) was placed in a 1.5 mL plastic conical vial. Citrate buffer pH 6.6 (50 µL of 0.1M) and $^{67}$gallium citrate (0.3 mL; 464 µCi) were added to this solution. The reaction mixture was stirred for 2 hours at 75 rpm. ITLC analysis were performed (acetone and normal saline elutions) and showed a reaction yield of 91.6%. The new $^{67}$gallium complex stays at the point of origin under these conditions while $^{67}$gallium citrate is eluted to the solvent front in acetonitrile.

b) at pH 7.7

In a 1.5 mL plastic conical vial, a solution of the bis-(2-hydroxybenzyl)bis-hydroxamic acid (33) (200 µL; ~4 µg/µL), 0.1M citrate buffer pH 7.7 (50 µL), and $^{67}$gallium citrate (0.3 mL; 450 µCi) were introduced. The reaction mixture was stirred for 2 hours at 75 rpm. ITLC analysis were performed (acetone and normal saline elutions) and showed a reaction yield of 100%. The new $^{67}$gallium complex stays at the point of origin under these conditions while $^{67}$gallium citrate is eluted to the solvent front in acetonitrile.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed:

1. A compound having the formula:

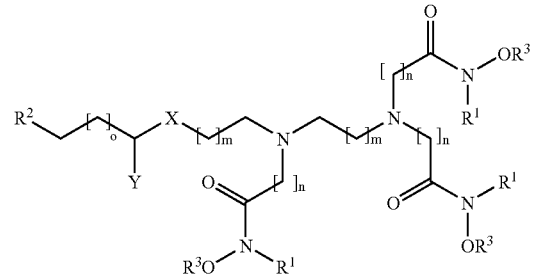

where:
- n, m and o are, independently, an integer from 1 to about 4;
- X is CH$_2$, N(R$^4$), oxygen or sulfur;
- Y is hydrogen, hydroxyl, =O N(R$^4$)(R$^5$), or =S;
- R$^1$ is hydrogen, alkyl having 1 to 5 carbon atoms, or a protective group;
- R$^2$ is an activated ester, a carboxylic acid, an alkyl isothiocyanate, an aromatic isothiocyanate or a leaving group;
- R$^3$ is hydrogen or a protective group;
- R$^4$ is hydrogen, alkyl having 1 to 5 carbon atoms, or a protective group; and
- R$^5$ is hydrogen, alkyl having 1 to 5 carbon atoms, or a protective group,
  wherein:
  said protective group is benzyloxycarbonyl or

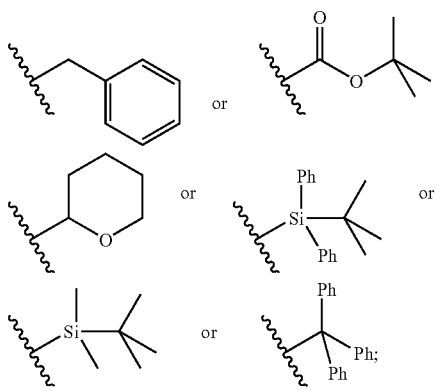

said activated ester is

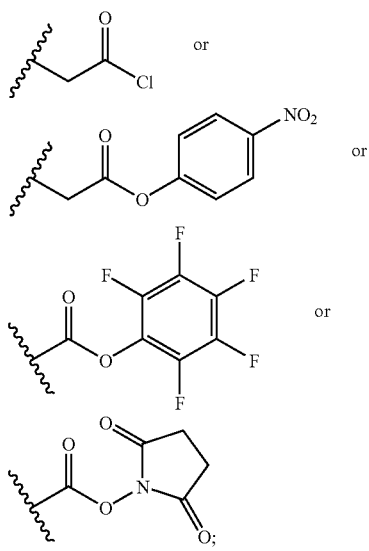

and
said leaving group is halo, mesylate, tosylate, or trifluorosulfonate.

2. The compound of claim 1 wherein the carboxylic acid group is:

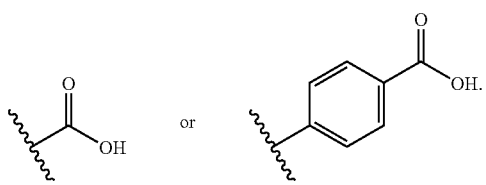

3. The compound of claim 1 wherein the isothiocyanato group is:

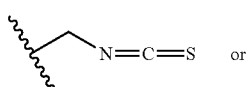

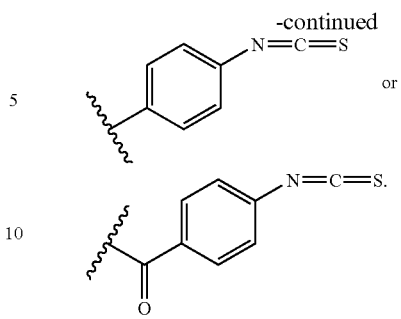

4. The compound of claim 1 wherein the protective group is tert-butoxycarbonyl or benzyloxycarbonyl.

5. The compound of claim 1 wherein n is equal to 1 or 2 and m is equal to 1 or 2.

6. The compound of claim 1 wherein:
n or m or o is 1 or 2;
X is $N(R^4)$ or oxygen;
Y is hydrogen or =O;
$R^1$ is hydrogen or methyl;
$R^2$ is p-nitrophenyl ester;
$R^3$ is hydrogen or tert-butyldiphenylsilyl; and
$R^4$ is methyl, ethyl, propyl or butyl.

7. A compound having the formula:

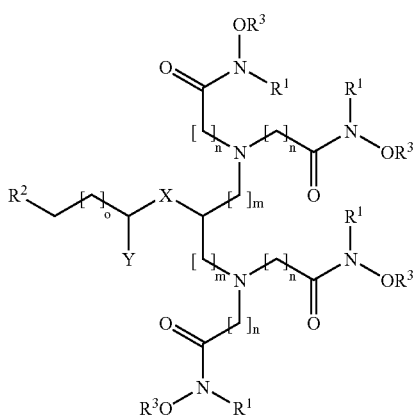

where:
n, m and o are, independently, an integer from 1 to about 4;
X is $CH_2$, $N(R^4)$, oxygen or sulfur;
Y is hydrogen, —OH, =O, $N(R^4)(R^5)$, or =S;
$R^1$ is hydrogen, alkyl having 1 to 5 carbon atoms, or a protective group;
$R^2$ is an activated ester, a carboxylic acid, an alkyl isothiocyanate, an aromatic isothiocyanate or a leaving group;
$R^3$ is hydrogen or a protective group;
$R^4$ is hydrogen, alkyl having 1 to 5 carbon atoms, or a protective group; and
$R^5$ is hydrogen, alkyl having 1 to 5 carbon atoms, or a protective group;
wherein
said protective group is benzyloxycarbonyl or

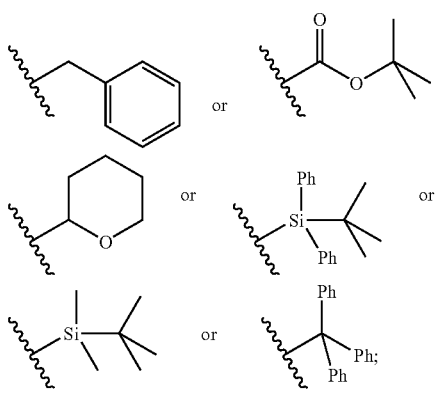

said activated ester is

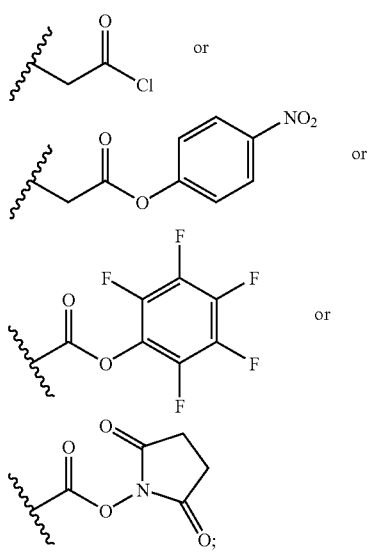

and said leaving group is halo, mesylate, tosylate, or trifluorosulfonate.

8. The compound of claim 7 wherein the carboxylic acid group is:

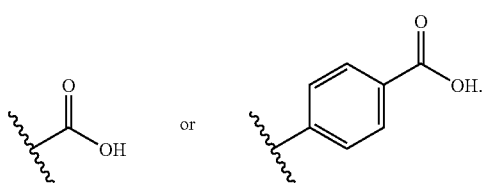

9. The compound of claim 7 wherein the isothiocyanato group is:

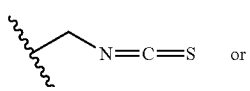

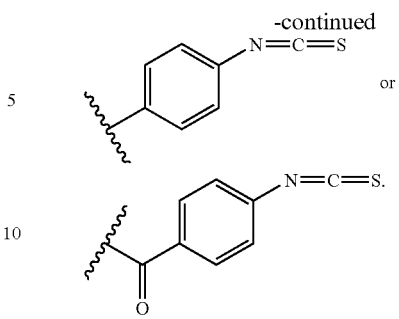

10. The compound of claim 7, wherein the protecting group is tert-butoxycarbonyl or benzyloxycarbonyl.

11. The compound of claim 7 wherein:

n or m or o is 1 or 2;

X is $N(R^4)$ or oxygen;

Y is hydrogen or carbonyl;

$R^1$ is hydrogen or methyl;

$R^2$ is p-nitrophenyl ester;

$R^3$ is hydrogen or tert-butyldiphenylsilyl; and $R^4$ is methyl, ethyl, propyl or butyl.

12. A compound having the formula:

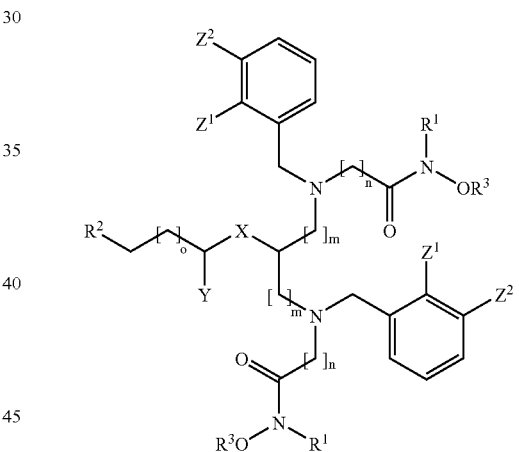

where n, m and o are, independently, an integer from 1 to about 4;

X is $CH_2$, $N(R^4)$, oxygen or sulfur;

Y is hydrogen, —OH, =O, $N(R^4)(R^5)$, or =S;

$R^1$ is hydrogen, alkyl having 1 to 4 carbon atoms, or a protective group;

$R^2$ is an activated ester, a carboxylic acid, or a leaving group;

$R^3$ is hydrogen or a protective group;

$R^4$ is hydrogen, alkyl having 1 to 5 carbon atoms, or a protective group;

$R^5$ is hydrogen, alkyl having 1 to 5 carbon atoms, or a protective group;

$Z^1$ is hydrogen, $N(R^4)(R^5)$, —OH, =O, or =S; and $Z^2$ is hydrogen, $N(R^4)(R^5)$, —OH, =O, or =S;

wherein said protective group is benzyloxycarbonyl or

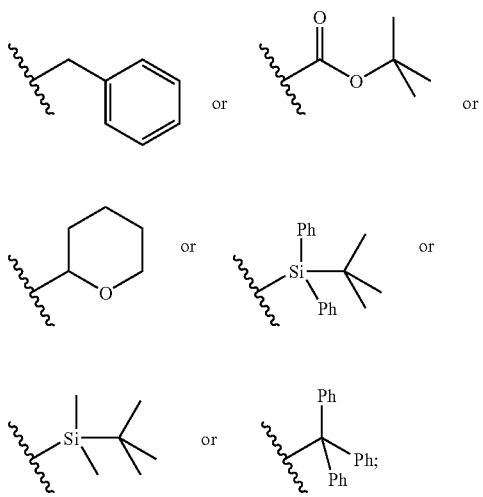

said activated ester is

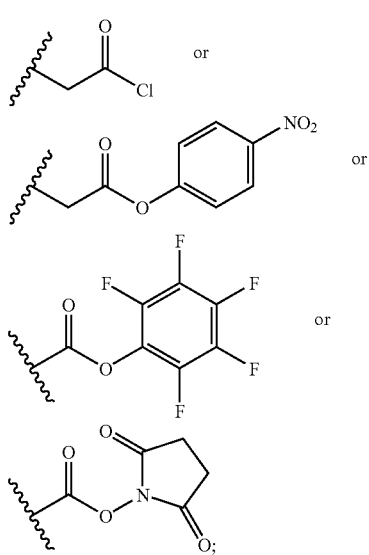

and
said leaving group is halo, mesylate, tosylate, or trifluorosulfonate.

13. The compound of claim 12 wherein the carboxylic acid group is:

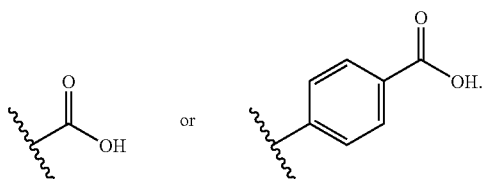

14. The compound of claim 12 wherein:
n or m or o is 1 or 2;
X is N($R^4$) or oxygen;
Y is hydrogen or =O;
$R^1$ is hydrogen or methyl;
$R^2$ is p-nitrophenyl ester;
$R^3$ is hydrogen or tert-butyldiphenylsilyl;
$R^4$ is methyl, ethyl, propyl or butyl;
$Z^1$ is —OH; and
$Z^2$ is hydrogen or —OH.

15. A pharmaceutical composition comprising a compound according to claim 1 in free or in pharmaceutically acceptable salt form and one or more pharmaceutically acceptable carriers or diluents.

16. A pharmaceutical composition comprising a compound according to claim 7 in free or in pharmaceutically acceptable salt form and one or more pharmaceutically acceptable carriers or diluents.

17. A pharmaceutical composition comprising a compound according to claim 12 in free or in pharmaceutically acceptable salt form and one or more pharmaceutically acceptable carriers or diluents.

18. The compound of claim 1 wherein:
said carboxylic acid is selected from the group consisting of

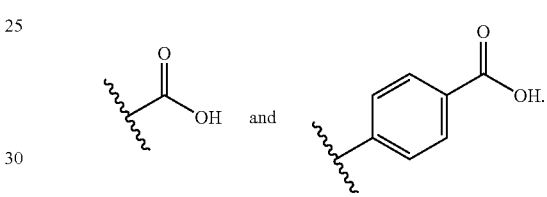

and
said isothiocyanate is selected from the group consisting of

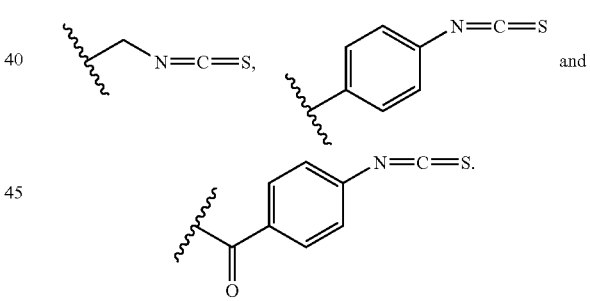

19. The compound of claim 7 wherein
said carboxylic acid is selected from the group consisting of

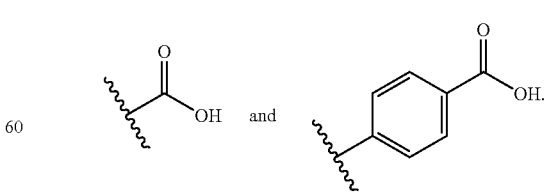

and
said isothiocyanate is selected from the group consisting of

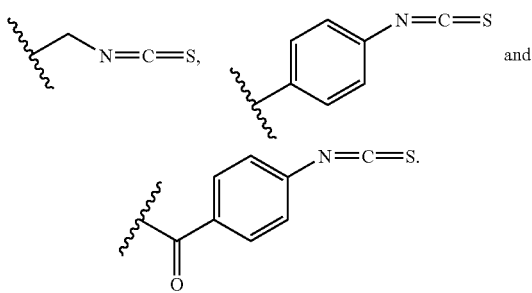

20. The compound of claim 12 wherein said carboxylic acid is selected from the group consisting of

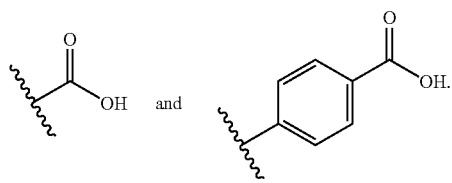

21. A method of treating a disease comprising administering to an animal in need thereof an amount of a compound according to claim 1 complexed with a radionuclide, wherein said amount is effective to treat the disease and the disease is selected from the group consisting of pituitary tumors, gastroenteropancreatic tumors, central nervous system tumors, breast tumors, prostatic tumors, ovarian tumors, colonic tumors, small cell lung cancer, paragangliomas, neuroblastomas, pheochromocytomas, medullary thyroid carcinomas, myelomas, metastases, or lymphomas.

22. A method of treating a disease comprising administering to an animal in need thereof an amount of a compound according to claim 7 complexed with a radionuclide, wherein said amount is effective to treat the disease and the disease is selected from the group consisting of pituitary tumors, gastroenteropancreatic tumors, central nervous system tumors, breast tumors, prostatic tumors, ovarian tumors, colonic tumors, small cell lung cancer, paragangliomas, neuroblastomas, pheochromocytomas, medullary thyroid carcinomas, myelomas, metastases, or lymphomas.

23. A method of treating a disease comprising administering to an animal in need thereof an amount of a compound according to claim 12 complexed with a radionuclide, wherein said amount is effective to treat the disease and the disease is selected from the group consisting of pituitary tumors, gastroenteropancreatic tumors, central nervous system tumors, breast tumors, prostatic tumors, ovarian tumors, colonic tumors, small cell lung cancer, paragangliomas, neuroblastomas, pheochromocytomas, medullary thyroid carcinomas, myelomas, metastases, or lymphomas.

* * * * *